United States Patent [19]
Chinnadurai

[11] Patent Number: 5,858,678
[45] Date of Patent: Jan. 12, 1999

[54] APOPTOSIS-REGULATING PROTEINS

[75] Inventor: Govindaswamy Chinnadurai, St. Louis, Mo.

[73] Assignee: St. Louis University, St. Louis, Mo.

[21] Appl. No.: 408,095

[22] Filed: Mar. 21, 1995

Related U.S. Application Data

[63] Continuation of Ser. No. 284,139, Aug. 2, 1994, abandoned.

[51] Int. Cl.$^6$ .............................. C07K 14/00; C12N 5/10; C12N 15/11; G01N 33/53
[52] U.S. Cl. ......................... 435/7.1; 435/365; 530/328; 530/329; 530/350; 536/23.5
[58] Field of Search ..................................... 530/324, 350, 530/328, 329; 435/4, 6, 7.1, 365; 436/86; 536/23.5

[56] References Cited

PUBLICATIONS

J. M. Boyd et al., "Bik, a novel death–inducing protein shares a distinct sequence motif with Bcl–2 family proteins and interacts with viral and cellular survival–promoting proteins", *Oncogene*, 11:1921–1928 (1995).

Z. N. Oltvai et al., "Bcl–2 Heterodimers In Vivo with a Conserved Homolog, Bax, That Accelerates Programed Cell Death", *Cell*, 74:609–619 (1993).

J. Boyd et al.; Adenovirus E1B kDa and bcl–2 Proteins Interact with a Common Set of Cellular Proteins, Oct. 21, 1994, Cell, vol. 79, pp. 341–351.

Eileen White; Life, death, and the pursuit of apoptosis, (Genes & Development) 1996, pp. 1–15.

K. Pun; Genbank submission, Jul. 31, 1995, Accession No. X89986, 2 pages.

J. Han; Genbank submission, Mar. 18, 1996, Accession No. U49730, 1 page.

J.M. Boyd et al., Genbank submission, Mar. 23, 1996, Accession No. 1235989, 2 pages.

Cleary et al. (1986) Cell 47:19–28, Oct. 1986.

Gingeras et al. (1982) J. Biol. Chem. 257:13475–13491, Nov. 1982.

Wilson et al. (1991) J. Exp. Med. 173:137–146, Jan. 1991.

*Primary Examiner*—George C. Elliott
*Assistant Examiner*—Robert Schwartzman
*Attorney, Agent, or Firm*—Sughrue, Mion, Zinn, Macpeak & Seas, PLLC

[57] ABSTRACT

Adenovirus E1B 19 kD protein protects against cell death induced by viral infection and certain external physical and chemical stimuli. Activity of the 19 kD protein is similar to the cell death suppressing activity of the protein coded by the Bcl-2 protooncogene. Bcl-2 protein can functionally substitute for the E1B 19 kD protein during adenovirus infection and in transformation of primary cells with adenovirus E1A. Five different cDNA's for proteins, designated Nip1, Nip2, Nip3, Bip1A and Bip13 that specifically interact with the 19 kD protein were found. Mutational analysis of the interaction indicates that at least four of the proteins (Nip1, Nip2, Nip3 and Bip1A) associate with 19 kD protein at specific sites thereof. Homologous motifs are found on Bcl2. An additional protein, (Bip5), interacts with Bcl-2 but not with the 19K protein.

17 Claims, 2 Drawing Sheets

FIG. 2A

RESIDUES 43-100 OF SEQ ID NO:21

```
Nip1     43  lntkvkekfqqlrhriqdleqlakeqdkesekqlllq..evenhkkqmlsnqaswrkanl  100
             :.|.:..|||:: .:|||: .|||: ||| ::...:.. ||| ::|.:.|..|
CaM-PDE 331  LATDMSCHFQQVKTMKTALQQLERI.DKSKALSLLLHAADISHPTKQ.WSWHSRWTKALM  388
                                                              SEQ ID NO:34
```

FIG. 2B

```
Consensus    O * O * O G * * O * * E
Nip2    79   E I D L D G L D T P S E    90  RESIDUES 79-90 OF SEQ ID NO:23
```

FIG. 2C

RESIDUES 168-299 OF SEQ ID NO:23

```
168  vvfevcfmpessqpnyrylmdnlfkyvigtlellvaenymivylngattrrkmpslgwlrkcyqqi  233
     :||.:||:|.:. :| .|: |:|:|||:|: ..:||: |.:|:::.:|:.:|.|::
 86  IVFSACRMPPSHQLDH...SKLLGYLKHTLDQYVESDYTLLYLHHGLTSDNKPSLWLRDAYREF  147

234  drrlrknlksliivhpswfirtllavtrpfisskfsqkiryvfnlaelaelvpmeyigipecikqv  299
     |::||:||:|| :|||:|: ||: |:|: |.|:.::|:.|:||.|| :|.| :::  :|.
148  DRKYKKNIKALYIVHPTMFIKTLLILFKPLISFKFGQKIFYVNYLSELSEHVKLEQLGIP...RQV  210
                                                              SEQ ID NO:35
```

APOPTOSIS-REGULATING PROTEINS

This is a Continuation of application Ser. No. 08/284,139 filed 2 Aug. 1994, abandoned.

This invention was made with government support under grant number CA-33616 awarded by the National Institutes of Health-National Cancer Institute. The government has certain rights in the invention.

BACKGROUND OF THE INVENTION

Apoptosis is a naturally occurring cell death characterized by reduction in cell volume, nuclear condensation, cell blebbing, and endonucleolytic degradation of DNA at nucleosomal intervals. The onset of apoptosis arises from an activation of one or more genetic programs. Apoptosis is distinct from cell necrosis where chromatin clumps, organelles swell and eventually the cell membrane dissolves (Edgington, 1993).

The 19 kD (19K) protein coded by the adenovirus (Ad) E1B region confers a survival function in adenovirus-infected cells and prevents premature cell death. The DNA fragmentation observed in cells infected with E1B 19K mutants is reminiscent of that observed during apoptosis (Wyllie, 1980). Hence, one can infer that the 19 kD protein protects against a cell death program induced by viral infection, thus facilitating efficient virus replication. The E1A proteins, and specifically the conserved region (CR) 1 and CR2 which interact with cellular proteins p300 and pRb and induce cellular proliferation, have been implicated in the onset of the virus-induced death program (White et al., 1991; Mymryk et al., 1994).

The 19 kD protein suppresses the cytotoxic effects of certain external stimuli such as tumor necrosis factor (TNF)-α (Gooding et al., 1991; White et al., 1992) and anti-Fas antibody (Hashimoto et al., 1991). Both TNF-α and anti-Fas have been shown to cause cell death through apoptosis (Laster et al., 1988; Itoh et al., 1991; Watanabe-Fukunaga et al., 1992). Similarly, the 19 kD protein protects cells against the effects of DNA damaging agents such as the anti-cancer drug cisplatin (Subramanian et al., 1993) and UV (Tarodi et al., 1993). Both cisplatin (Sorenson & Eastman, 1988) and UV (reviewed by Williams, 1991) induce cell death through the apoptotic pathway.

Levels of p53 increase in response to DNA damaging agents and it appears that the accumulation of p53 is responsible for the induction of apoptosis by DNA damaging agents (Clarke et al., 1993; Lowe et al., 1993; Lane, 1993). Since 19K can efficiently suppress cell death induced by DNA damaging agents (Subramanian et al., 1993; Tarodi et al., 1993), it appears that 19K suppresses p53-dependent apoptosis (Debbas and White, 1993). Thus, the 19 kD protein provides a survival function in virus-infected cells and also protects cells against certain other cell death-inducing stimuli.

The survival function provided by E1B 19K appears to be strikingly similar to the activity of the cellular proto-oncogene, bcl-2. The bcl-2 oncogene enhances the survival of hematopoietic B and T cells by blocking apoptosis (Vaux et al., 1988; Sentman et al., 1991; Strasser et al., 1991). Overexpression of Bcl-2 protein inhibits apoptosis induced by treatment with glucocorticoids (Alnemri et al., 1992a), deprivation of cytokines (Nunez et al., 1990; Hockenbery et al., 1990), activation of the c-myc oncogene (Bissonnette et al., 1992; Fanidi et al., 1992), radiation (Strasser et al., 1991) and other DNA damaging agents (Tarodi et al., 1993).

Thus, Bcl-2 appears to protect against apoptosis induced by diverse agents. The effect of the 19 kD protein on cell death induced by such a multitude of stimuli has yet to be examined. However, it is known that the Bcl-2 protein can substitute for the 19 kD protein during adenovirus infection. The characteristic fragmentation of cellular DNA induced by infection with Ad2 19K mutants is suppressed in cells expressing the human Bcl-2 protein (Tarodi et al., 1993). Similarly, expression of Bcl-2 by an adenovirus 2/Bcl-2 recombinant virus does not induce DNA fragmentation in infected cells and forms small plaques on cell monolayers. Rao et al. (1992) reported that Bcl-2 can substitute for 19K, albeit at reduced levels, in transformation of primary rat kidney cells in cooperation with E1A.

Studies have indicated that there are a number of molecules with homology to and that have similar activities with bcl-2. Hence, there might be termed an assemblage of functionally related molecules which includes BHRF-1, bcl-$X_L$, bcl-$X_s$, mcl-1 and the like. The similarity can extend to a structural homology at the nucleic acid level, protein level or both. But as will be revealed hereinbelow, the homology need not be over the length of the molecule but can be confined to discrete functional portions of the molecule. Hence, under that criterion, 19K also comprises the assemblage of molecules relating to apoptosis.

The mechanism by which the 19K gene and the Bcl-2 protooncogene protect against cell death is not known. It is possible that those apoptosis-regulating proteins (hereinafter blocking proteins) mediate cell survival by interacting with certain cellular apoptosis-regulating proteins. Identification of any such cellular apoptosis-regulating proteins which interact with E1B 19 kD protein and with Bcl-2 would enable regulation of apoptosis in cells.

SUMMARY OF THE INVENTION

An object of the instant invention is to provide proteins, and the nucleic acids encoding said proteins, which bind to proteins known to regulate cell survival.

Another object of the instant invention is to provide oligopeptides, and the nucleic acids encoding said oligopeptides which mediate the interaction between proteins of the instant invention and proteins known to regulate cell survival.

Yet another object of the instant invention is use of said proteins and oligopeptides which bind to proteins known to regulate cell survival in diagnostic assays to assess presence and activity of said cell survival regulating proteins.

Those and other objects have been achieved in the identification of a series of proteins which bind to the E1B 19K and Bcl-2 proteins, and in the identification of consensus sequences shared by the proteins which mediate the binding therebetween.

BRIEF DESCRIPTION OF THE DRAWINGS

FIGS. 2A, 2B and 2C depict sequence homologies. FIG. 2A Homology between Nip1 (amino acids 43–100 of SEQ ID NO:21) and the catalytic domain of rat oalmodulin (CaM)-dependent phosphodiesterase (PDE) (SEQ ID NO:34) (Repaske et al., 1992). Similar homologies are also observed with mouse and cattle PDE's.

FIG. 2B Putative $Ca^{2-}$-binding motif of Nip2 (amino acids 79–90 of SEQ ID NO:23). O indicates an oxygen-containing residue, * indicates non-conserved residues and underlined residues are those that conform to the consensus.

FIG. 2C Homology between Nip2 (amino acids 168–299 of SEQ ID NO:23) (lower case letters) and human GTPase activating protein, RhoGAP (SEQ ID NO:35), Barfod et al., 1993; Lancaster et al., 1994).

DETAILED DESCRIPTION OF THE INVENTION

Figure 1:
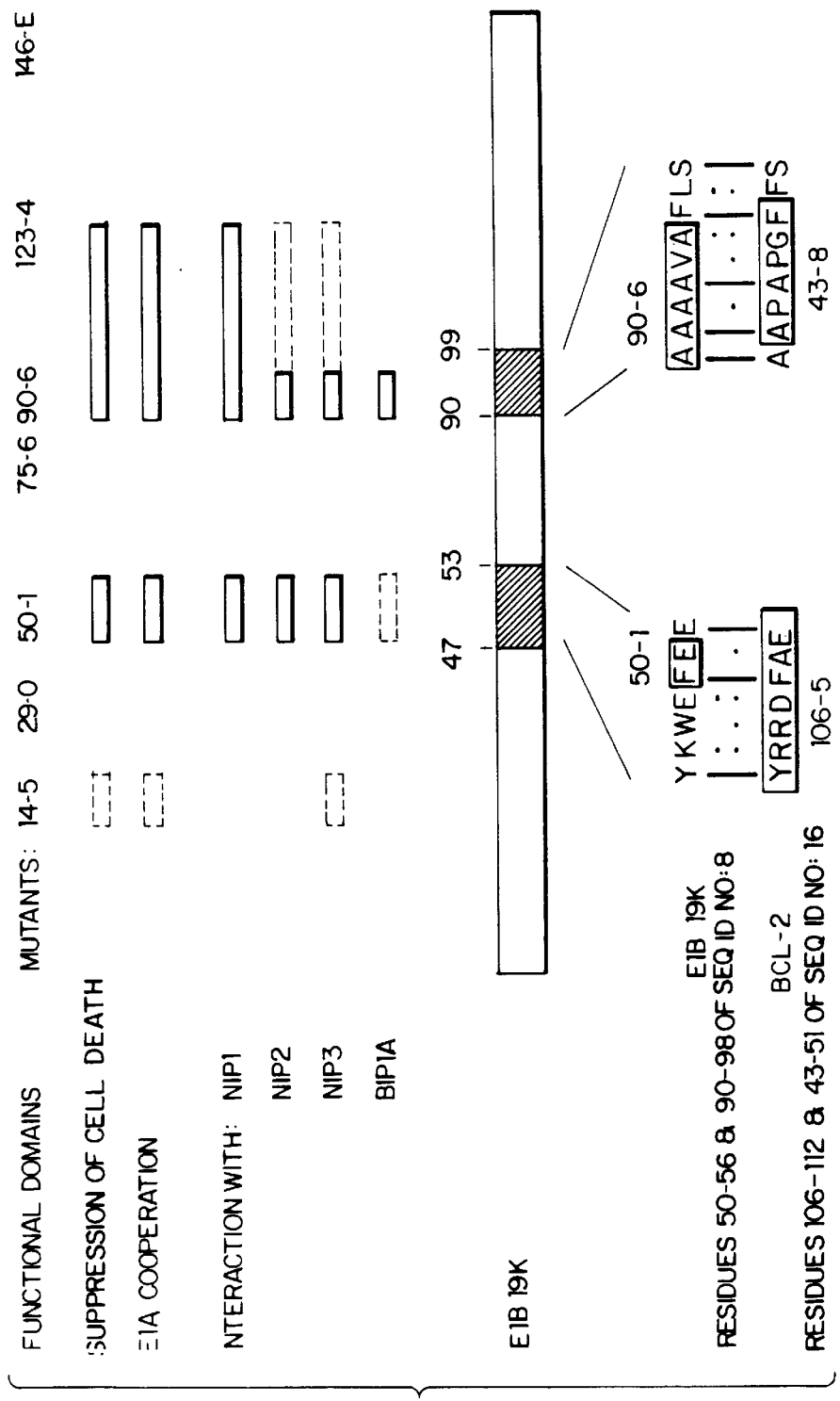
FIG. 1 depicts the functional organization of the 19 kD protein. The 19 kD sequences involved in suppression of cisplatin-induced cell death and E1A-cooperative transformation are based on Subramanian et al. (1993). In the top half of the figure, solid line bars indicate strong effects of various mutants on the 19 kD functions and interaction with cellular proteins, bars with dashed lines indicate weak effects. The sequence similarity between the 19 kD and Bcl-2 proteins and the mutants that map within those sequences (set off in boxes) are shown at the bottom of the figure (residues 50–56 of SEQ ID NO:8, residues 90–98 of SEQ ID NO:8, residues 106–112 of SEQ ID NO:16 and residues 43–51 of SEQ ID NO:16, respectively). The human Bcl-2 protein is a mutant form isolated from a human lymphoma and contains a Phe (instead of Ile) residue at position 48 (Seto et al. 1988, Hockenbery et al., 1990) and two other mutations (Seto et al., 1988). Identical amino acids are indicated by solid lines, similar amino acids by colons and distantly related amino acids by single dots.

Isolated, in the context of the instant invention, indicates that some intervention occurs which increases the level of purity of a molecule over that found in nature.

Derivatives in the context of the instant invention is contemplated to include any modifications to the molecules of interest, including truncation, fusion, complexing to carriers and the like which brings about a physical change in the parent molecule but does not alter substantially the biologic function thereof in relationship to the parent molecule. Biologic function may be enhanced or may be lowered so long as a desirable and tolerable level is maintained. A lowered activity is palatable when a subsidiary characteristic is enhanced, for example, solubility in an aqueous medium. Alternatively, a change in the sequence that gives a mutant may yield activity that is opposite of that of the parent molecule.

It should be noted that sequence identity whether at the peptide or nucleic acid level, while preferred under certain circumstances, is not a sine qua non condition in the instant invention. A key determinant, thus, is not the absolute sequence per se but the function ascribed to the molecule or to a product of the molecule. Hence, functional equivalence is the guiding directive as to the molecules of the instant invention.

Accordingly, by way of example, any one or all of the amino acids in the motifs described herein can be substituted so long as binding activity with the target of the parent sequence is retained. As noted hereinabove, as to the level of binding, that degree is mandated by the design, choice and end use of the motif derivative, and the artisan can configure and determine same without undue experimentation practicing the methods set forth herein.

The instant active agents regulate cell survival, that is, cell survival can be enhanced or prolonged or cell survival can be curtailed or shortened.

As noted hereinabove, there are molecules which have the effect of prolonging cell survival. Examples are Bcl-2 and E1B 19K. Such proteins appear to subvert apoptosis and thereby prolong cell survival. To prolong cell survival is to generate cells that statistically survive longer than expected.

The in vivo genetic strategy designated 'two hybrid' cloning (Fields and Song, 1989; Chien et al., 1991) permits rapid genetic screening in yeast of molecules that associate and the method has been used to isolate from expression libraries cDNA clones that code for proteins interacting with several known proteins.

Briefly, the method relies on the double transformation of yeast hosts with plasmids that encode fusion proteins. One plasmid carries partial sequences for a reporter molecule, for example, the GAL4 DNA binding domain, at the amino terminus of the fusion protein and sequences for the known protein, to which a ligand is sought, also known as the "bait" at the carboxyl terminus. For example, the bait can be the 19K protein or Bcl-2 protein.

The second plasmid comprises sequences encoding a complementary protein for the reporter molecule, in the above case, required by the GAL4 DNA binding domain, such as the GAL4 activation domain, at the amino terminus and expressed products of individual cDNA's from a bank at the carboxyl terminus. A suitable host is used to enable the selection planned, in the scenario discussed, the host would be one wherein the expression of β-galactosidase is under the control of the GAL1 promoter.

Selection of double transformants are those that express β-galactosidase, hence would be blue colonies on an X-gal plate because the bait and protein encoded by the cDNA of the second plasmid bind and that interaction juxtaposes the two GAL4 regulatory elements required for β-galactosidase expression.

In the case where 19K or Bcl-2 is the bait, the cDNA's identified thereby, encode polypeptides that bind 19K, Bcl-2 or both. Hence, those proteins have a key role in apoptosis whether by functionally and directly regulating one or more of the observable characteristics (symptoms) of apoptosis or by affecting the survival enhancing activity of 19K or Bcl-2, possibly by binding thereto.

As is known in many biologic systems, because of the tertiary and quaternary configuration of molecules and the interactions therebetween, often small portions of a molecule can have key functions, such as a recognition function, a signalling function, a catalytic function, a binding function and the like. For example, a specific antigenic determinant may comprise as few as five to six contiguous amino acids of a polypeptide and the variability and diversity of antibodies is generated by a non-contiguous plurality of short amino acid stretches in the heavy and light chains that vary from clone to clone.

Similarly, the binding interaction of an apoptosis-regulating protein, such as 19K and bcl-2, with another apoptosis-regulating molecule, such as Nip1, Nip2, Nip3 and Bip1A, disclosed herein, is governed and mediated at least in part by certain sites of the proteins which are contiguous portions of the proteins which comprise short conserved motifs or consensus sequences of amino acids. The motifs can comprise 15 amino acids or less, often 10 amino acids or less. Two motifs are AAPAPGFFS (SEQ ID NO:1) and YRRDFAE (SEQ ID NO:2) of Bcl-2 and YKWE-FEE (SEQ ID NO:3) and AAAAVAFLS (SEQ ID NO:4) of 19K. Those sequences play crucial roles in the interaction between regulating molecules. Related sequences, e.g., Ybx-aFxE (SEQ ID NO:5), where b is a basic amino acid, x is any amino acid and a is an acidic amino acid, and AAhAhFhS (SEQ ID NO:6), where h is a hydrophobic amino acid, may be important for the interaction as well.

It is likely that mutation at the site of the motif can have consequences related to the normal functioning of the apoptosis regulating molecules and interaction therebetween. For example, the motif from a normal B cell clone of Bcl-2 was found to be AAPAPGIFS (SEQ ID NO:7) (Cleary, 1986). On the other hand, the motif obtained from a follicular lymphoma-derived clone of bcl-2 was found to be AAPAPGFFS (SEQ ID NO:1). Also, the bcl-2 consensus may endure some variability having a sequence YRGDFAE (SEQ ID NO:32) (Tsujimoto & Croce, 1986).

That observation demonstrates the importance of the consensus sequence in the normal state and provides a differential marker for identifying and screening abnormal cells based on the amino acid substitution.

The instant nucleic acids and polypeptides may be obtained as described herein, that is by recombinant means, or may be used to obtain homologous nucleic acids and proteins by hybridization, for example, an instant nucleic acid can be used as a probe of a gene bank to identify clones with suitable homology therewith. Also, within the confines of available technology. The nucleic acids and polypeptides may be synthesized in vitro using, for example, solid phase oligonucleotide and oligopeptide synthetic methods known in the art.

The interactions between the apoptosis-regulating proteins, such as 19K and Bcl-2, and the proteins of the instant invention that bind thereto may take a variety of forms. For example, the molecules may either promote or suppress apoptosis on their own. The 19K and Bcl-2 type proteins may recruit the proteins of the instant invention and promote cell survival by enhancing the activity thereof or by suppressing the activity thereof.

The availability of ready sources of apoptosis-regulating proteins enables the manipulation of cells for a desired purpose. For example, it is believed that certain malignancies arise from over-expression of an apoptosis-blocking gene, such as bcl-2. In that case, application or administration of an instant protein, or nucleic acid encoding said protein, can counteract the high levels of Bcl-2. In the converse, application or administration of a protein such as Bcl-2 will enhance the life span of a cell.

Hence, the instant proteins find utility in the growth and maintenance of cells and tissues in culture. The instant proteins can be added to the culture medium in similar fashion to those supplements now used, such as, fetal calf serum, glutamine and the like. Whether an inducing or blocking molecule is used will depend on the needs of the investigator and the cell or tissue cultured.

The instant proteins that enhance cell survival can be used to maintain valuable cells without the usual "malignant" transformation methods now used. Hence, culture medium can contain one or more of the instant proteins or cells can be transfected by an expressable nucleic acid encoding the desired protein(s). Such a transfection can be by known means, such as microinjection or by precipitation, and the vector can be one which is retained episomally or integrates into the host genome. The vector comprises known regulatory elements, including optionally a signal sequence nucleic acid fragment, to ensure proper expression, such as a promoter, enhancer, terminator and the like. The starting materials and methods are available in the art.

It is evident that the instant molecules can find utility in vivo using those administration means found suitable for oligopeptides, proteins and nucleic acids. The instant molecules may be encapsulated, for example, in a liposome or in an implantable depot to overcome some of the known administration problems which might confound adequate delivery and activity at a site. Moreover, the instant molecules may be conjugated to cell binding molecules for direct targeting to a site.

The uses of the instant molecule are contigent on the impact thereof on cell survival. The use of biologics in pharmaceutic preparations is known in the art. Hence, the instant molecules could find application in treatment and amelioration of immune disorders, abnormal states characterized by aberrant cell growth and the like.

The instant molecules of apoptosis-regulating activity find utility in diagnostic assays for the presence and expression of relevant nucleic acids, presence and expression of relevant proteins, presence and functionality of binding between the two classes of molecules and the like. Use of, for example, the oligopeptide motifs in a solid-phase microassay would enable identifying whether functional apoptosis-regulating molecules are present in a sample. Hence, expression and extracellular presence of apoptosis-regulating proteins in degenerative diseases, such as Alzheimer's disease and spina bifida, may be diagnositic of those disorders.

Hence, the instant motif oligopeptides can be affixed to a solid phase, such as plastic microtiter dishes, using methods obtained from immunology for the fixing of antigen or antibody to a plate and then a sample is added. Following suitable washes, the presence of and amount of bound material is assessed, for example using a labelled antibody specific for the apoptosis-regulating molecules and the amount of label is assessed. Alternatively, the assessment can be visual under a microscope and the like. Alternatively, the motif can be labelled, applied to a sample and the label present assessed, similar to known radioreceptor assays, such as those for hormones using the hormone receptor as a specific reporter.

Such an assay which turns on the functional association between an apoptosis regulating molecule can be beneficial in identifying drugs that impede or prevent the interaction of the apoptosis regulating molecules.

As disclosed herein, some of the instant proteins bear homology to known proteins with a characteristic biologic activity. Hence, presence and amount of an apoptosis-regulating molecule can be ascertained by assaying for that biologic activity. For example, if a regulating molecule has enzymatic activity, then an assay for the presence and amount of that regulating molecule may rely on the assay of that enzymatic activity.

Hence, the amount of apoptosis-regulating molecules now can be ascertained in a sample using either of the two binding molecules as a receptor for the other.

Alternatively, rather than monitoring presence of the relevant molecules by physical characterization, for example, electrophoresis, or by activity, for example, an assay of an enzymatic activity, the instant molecules can be ascertained indirectly by ligands other than one or the other, for example, a ligand such as a lectin or an antibody.

As to antibodies, such specific reagents can be made using known techniques and using the target molecule as antigen. If the target molecule is poorly immunogenic, known methods for enhancing immunogenicity, such as, use of adjuvants, use of fragments of the target molecule as antigen, conjugating the target molecule or fragments thereof to a known carrier, such as albumin or keyhole limpet hemocyanin, immunizing immune cells in vitro and the like, as known in the art can be used. Either polyclonal or monoclonal antibodies can be made. For example, the 2G9 antibody reacts with the 15 kd TIA-1 protein which is related to apoptosis (Tian et al., 1991). Thus, by obtaining and using such antibodies, presence and amount of a target molecule can be determined using any of the known immunoassay formats.

The invention now will be described by reference to the following non-limiting examples.

EXAMPLE 1

A fusion protein consisting of the yeast GAL4 DNA-binding domain (amino acids 1–147) and E1B 19 kD protein (residues 2–175) expressed from a yeast shuttle vector (pMA424-19K or pAS-19K) was used as a bait in the two hybrid screen. The DNA sequences coding for the bait proteins were generated by PCR and cloned between the unique EcoRI and BamHI sites of pMA424 and pAS1 in the case of 19 kD (or between the EcoRI and SalI sites in the case of Bcl-2).

Plasmids expressing the 19 kD bait and a human cDNA expression library designated pACT (Durfee et al., 1993) tagged with the GAL4 activation domain (Durfee et al., 1993) were used for simultaneous transformation of yeast indicator strains, GGY1::171 (Gill and Ptashne, 1987) or Y153 (Durfee et al., 1993) by the lithium acetate method of Schiestl & Giest (1989). Functional reconstitution of the GAL4 transactivation function through interaction between the 19 kD moiety of the GAL4(1–147)-19K fusion protein and the cellular protein tagged with the activation domain of GAL4 activates expression of the lacZ reporter gene in strain GGY1::171 and both the HIS3 and lacZ genes in strain Y153.

Transfected cells were plated on synthetic dropout medium (SD), Rose et al., 1990, lacking leucine and histidine (strain GGY::171) or lacking histidine, tryptophan and leucine (strain Y153) by including 12.5 to 25 mM 3-AT 3-aminotriazole, a chemical which restores histidine auxotrophy (Kishore and Shaw, 1988). After three (GGY::171) to five (Y153) days at 30° C., colonies were lifted onto nitrocellulose filters (Schleicher and Schuell, BA85) and made permeable by freezing the filters for 5–10 sec on aluminum foil floats placed over liquid nitrogen.

Filters were overlaid on Whatman filters saturated with Z buffer (Miller, 1972) containing 1 mg/ml X-Gal and incubated at 30° C. (Breedan and Nasmyth, 1985). Colonies which turned blue within a period of 1–6 hr were picked and patched onto fresh selective plates.

The cells then were diluted in TE (10 mM Tris, pH 8.0 and 1 mM EDTA), plated onto selective plates and well-isolated colonies which were positive in the X-Gal assay were selected. Cells from the isolated colonies were patched onto selective plates and were then grown in selective liquid SD media. After overnight growth, the plasmid DNAs were extracted from the cells using glass beads (Hoffman and Winston, 1987) and the recovered DNA was used to transform an *E. coli* leuB strain (obtained from Stanley Fields, S.U.N.Y. Stony Brook) by electroporation using a BRL Cellporator according to the specifications of the manufacturer.

Ampicillin-resistant colonies were selected and replica plated on minimal M9 plates lacking amino acids to eliminate the plasmid expressing the bait protein. Plasmid DNA (containing the LEU marker) from colonies which grew on M9 media was prepared by alkaline lysis. The interaction between the 19 kD protein and the proteins coded by the cDNA clones was further ascertained by a second round of yeast transformation and X-gal staining. The cDNA clones which were positive with pMA-19K or pAS-19K and not with pMA424 or pAS1 vectors were selected for further analysis. The interaction of the selected cDNA clones with various heterologous protein baits then was determined to further ascertain the specificity of interaction with the 19 kD bait.

About $10^5$ transformants of each strain were screened for the activation of the reporter genes and three strongly positive clones were chosen for further analysis. The clones were tested in the two hybrid screen with either the 19K bait or with the GAL4 DNA binding domain vectors, pMA424 (Ma & Ptashne, 1987) or pAS1 (Durfee et al., 1993). All three clones (22, 44 and 91) reacted positively only with the 19K bait and not with the respective vectors.

The three clones (22, 44 and 91) were found to be defective in interaction with 19K mutant baits of interest.

EXAMPLE 2

To determine the specificity of the two hybrid interaction, the three clones, 22, 44 and 91, were tested against baits expressing several heterologous proteins (Table 1). Among the various heterologous protein baits used, the adenovirus E3 11.6 kD protein is of particular interest as that protein localizes on the nuclear envelope region and has an internal hydrophobic domain like the E1B 19 kD protein (Scaria et al., 1992). All three clones were negative against all the heterologous protein baits tested, indicating that the proteins coded by the clones specifically interact with the 19 kD protein.

TABLE 1

Interaction of cellular apoptosis-regulating proteins with heterologous protein baits[@]

| | lacZ expression (X-gal) | | |
|---|---|---|---|
| Bait | clone 22 | clone 44 | clone 91 |
| 19 kD | B | B | B |
| HIV-1 Rev | W | W | W |
| HIV-1 Tat | W | W | W |
| HIV-1 Nef | w | w | W |
| HTLV-I Rex | W | W | W |
| SNF1 | ND | W* | W* |
| E1A-Exon2 | W | W | W |
| h-1amin | W | W | W |
| E3-11.6 kD | W | W | W |

B = Blue
W = White
[@]Interactions with all baits except the yeast SNF1 protein were carried out in yeast Strain GGY1::171. Interaction with SNF1 was carried out in yeast strain Y153.
*Colonies which appeared on -his, -trp, -leu plates after 6–8 days. Results of X-gal staining are indicated as B, blue; W, white; or ND, not done.
The heterologous baits pLAM5 (human lamin) and pAS-SNF1 (yeast SNF1) have been described (Bartel et al., 1993, Durfee et al., 1993). Baits pHIV-1 Rev, pHIV-1 Tat, pHIV-1 Nef and pHTLV-1 Rex expressing the various HIV or HTLV regulating proteins were constructed as described herein and obtained from Cleta D'Sa Eipper and T. Subramanian, St. Louis University Medical Center, St. Louis, MO.

EXAMPLE 3

Proteins coded by the various cDNA clones were prepared by in vitro transcription and translation using the phage T7-based expression vector, pET3b (Studier et al., 1990) and a commercially available kit (Promega, Madison, Wis.). $^{35}$S-labeled proteins coded by clones 22, 44 and 91 were incubated with protein extracts prepared from human 293 cells (Graham et al., 1977) which express abundant amounts of 19 kD protein or extracts of HeLa cells which do not express any adenovirus proteins. The interaction of the labeled proteins with the 19 kD protein then was analyzed by immunoprecipitation with an antibody specific for the 19 kD protein (Green et al., 1982). The 293 cell extract was used as a source of 19 kD protein rather than purified protein since the cell extract may be suitable to detect interaction of exogenously added proteins with 19 kD protein if the interaction occurs indirectly via other cellular proteins.

Exogenously added $^{35}$S-labeled proteins coded by both clones readily were precipitated with 19K antibodies in the presence of 293 cell extracts. Under the same binding conditions, $^{35}$S-labeled luciferase (control) was not precipitated. Similarly, no significant amounts of the various labeled proteins were precipitated from HeLa cell extracts.

In all cases, immunoprecipitations with normal rabbit serum also did not precipitate any detectable levels of the proteins.

The results indicate that the proteins coded by clones 22, 44 and 91, (hereafter referred to as 19K-interacting protein (Nip) 1, Nip2 and Nip3, respectively) specifically interact with the 19 kD protein either directly or indirectly and substantiate the results obtained by the two hybrid screens.

EXAMPLE 4

To confirm the interaction of the Nip proteins with the 19 kD protein in vivo, BSC40 were transfected with plasmid vectors expressing the 19 kD or various Nip proteins under the transcriptional control of the T7 promoter in a mammalian expression vector, pTM1 (Moss et al., 1990). The cells were infected with the recombinant vaccinia virus vTF7-3 expressing the T7 RNA polymerase gene (Fuerst et al., 1986) to induce the expression of proteins from the various pTM1 plasmids. To facilitate the analysis of protein interactions, the Nip proteins were tagged with an epitope corresponding to a 9 amino acid region of the haemagglutinin (HA) protein of influenza virus (Field et al., 1988). The pTM1 vector expressing only the HA epitope was used as a control.

Cells were labeled in vivo with a $^{35}$S-methionine and $^{35}$S-cysteine mixture, lysed and the lysates divided and subjected to immunoprecipitation analysis using either a monoclonal HA antibody 12CA5 (Boehringer-Mannheim, Indianapolis, Ind.) or a 19 kD antipeptide antibody (Green et al., 1982). The precipitated proteins were analyzed by SDS-PAGE and autoradiography to determine whether comparable levels of the 19 kD protein were present in each sample. The HA immunoprecipitates were separated by SDS-PAGE, blotted onto nitrocellulose and probed with the 19 kD antibody to detect the presence of coprecipitating 19 kD protein. A horseradish peroxidase-chemiluminescent detection system (ECL) (Amersham, Arlington Heights, Ill.) was used to visualize bound antibodies.

The 19 kD protein was not detected in HA immunoprecipitates from cells transfected with the pTM1-HA vector and pTM1-19 kD, but clearly was seen coprecipitating with HA-tagged Nip1, Nip2 and Nip3.

Cells also were cotransfected with plasmids expressing each of the Nip proteins and either the 19 kD or the vector plasmid. Cell lysates were immunoprecipitated with the 19 kD antibody, blotted and probed with anti-HA antibody. That experimentation yielded comparable results for Nip1 and Nip3 (Nip2 is not transfered to nitrocellulose under standard blotting conditions) and provides additional support for the specificity of the interactions.

The results indicate that the 19 kD protein interacts specifically with each of the Nip proteins in an in vivo immunoprecipitation assay.

EXAMPLE 5

To determine the subcellular localization of the 19 kD-interacting proteins and to investigate whether the proteins colocalize with the 19 kD protein within the cell, COS7 cells (Gluzman, 1981) with plasmids expressing the protein coding sequences of the cDNA clones either alone or with a 19 kD-expressing plasmid were overturned and the transfected cells were analyzed by indirect immunofluorescence. To facilitate the immunofluorescence analysis of the 19 kD-interacting proteins, the proteins first were tagged with an epitope corresponding to a 9 amino acid region of the hemagglutinin (HA) protein of influenza virus (Field et al., 1988).

The cDNA's were cloned into the expression plasmid pCMV-HA which tags the proteins with an HA epitope. COS7 cells, grown on 22 mm$^2$ coverslips in 30 mm dishes, were transfected with plasmids expressing the 19 kD protein (pRcCMV-19K) and/or each of the pCMV-HA based cDNA clones using the LipofectAMINE™ reagent (Gibco-BRL) following the manufacturer's protocols. Forty eight hours post-transfection cells were fixed with 3.7% formaldehyde in PBS and permeabilized with ice-cold methanol. Cells were double stained with mouse monoclonal anti-HA (Berkeley Antibody Co., Inc.) and rabbit polyclonal anti-19 kD peptide serum (Green et al., 1982), and visualized with goat anti-rabbit rhodamine conjugate (Cappel) and goat anti-mouse fluorescein conjugate (Pierce). Cells were observed and photographed for rhodamine (19 kD) and fluorescein (HA-tagged clones) fluorescence. The localization of each cellular protein was examined in the absence of or presence of the 19 kD protein. The 19 kD protein primarily was expressed at the nuclear envelope/endoplasmic reticulum region. Nip1 (clone 22) and Nip2 (clone 44) also appear to be concentrated primarily on the nuclear envelope region in addition to other cytoplasmic structures. Nip3 (clone 91) has a different pattern of localization having a punctate pattern resembling the patterns exhibited by mitochondria (Alberts et al., 1989).

In cells coexpressing Nip1, Nip2 or Nip3 and the 19 kD protein, both the 19 kD and each of the cellular proteins colocalized primarily at the nuclear envelope region. Hence, the apoptosis-regulating cellular proteins localize identically with the 19 kD protein, which includes a marked shift in the localization pattern of Nip3.

EXAMPLE 6

The two hybrid strategy provides a rapid method for genetic analysis of in vivo protein-protein interaction. A series of 19K mutants (Table 2) with regard to ability to protect against cell death induced by the DNA damaging agent cisplatin and to cooperate with E1A in transformation of primary cells were used (Subramanian et al., 1993). The wild type 19K sequence is identified as SEQ ID NO:8; the 14-5 mutant as SEQ ID NO:9; the 29-0 mutant as SEQ ID NO:10; the 50-1 mutant as SEQ ID NO:11; the 75-6 mutant as SEQ ID NO:12; the 90-6 mutant as SEQ ID NO:13; the 123-4 mutant as SEQ ID NO:14; and the 146-E mutant as SEQ ID NO:15.

In Table 2 the names of the various mutants are marked above the amino acid sequence and the amino acid changes are indicated below the sequence. The actual amino acids involved in the various mutations are indicated in boldface. Z indicates a stop codon. Δ indicates deletion. The underlined sequence is homologous to conserved domain I of bcl-2 (Williams & Smith, 1993).

TABLE 2

19K and Bcl-2 Mutants

E1B 19K

```
                 14-5                      29-0                          50-1
  1  MEAWECLEDFSAVRNLLEQSSNSTSWFWRFLWGSSQAKLVCRIKEDYKWEFEELLKSCGE
                  AS                        AS                           AS 75-6                    90-6
 61  LFDSLNLGHQALFQEKVIKTLDFSTPGRAAAAVAFLSFIKDKWSEETHLSGGYLLDFLAM
              AS                       Δ

123-4                                   146-E
121  HLWRAVVRHKNRLLLLSSVRPAIIPTEEQQQEEARRRRRQEQSPWNPRAGLDPRE
           AS                         SZ
```

Bcl-2 (Seto et al., 1988)

```
                                                             42-8
  1  MAHAGRSGYDNREIVMKYIHYKLSQRGYEWDAGDVGAAPPGAAPAPGFFSSQPGHTPHPA
                                                              Δ

80-6                                        106-5
 61  ASRDPVARTSPLQTPAAPGAAAGPALSPVPPVVHLTLRQAGDDFSRRYRRDFAEMSSQLH
                   Δ                                           Δ

121  LTPFTARGCFATVVEELFRDGVNWGRIVAFFEFGGVMCVESVNREMSPLVDNIALWMTEY

181  LNRHLHTWIQDNGGWDAFVELYGPSMRPLFDFSWLSLKTLLSLALVGACITLGAYLGHK
```

The 19K-coding regions of the mutants were cloned in the pMA424 vector and tested for ability to interact with Nip1, Nip2 and Nip3 in the two hybrid assay. The interaction was assessed by determining the level of lacZ expression by the X-gal filter blue/white color assay as well as by a quantitative ONPG-based β-galactosidase assay (Rose et al., 1990) (see Table 3).

TABLE 3

Interaction of cellular apoptosis-regulating proteins with 19K mutants

| Mutant | Cell death suppression[@] | Interaction with cellular proteins (Relative level of lacZ expression) | | | | | |
|---|---|---|---|---|---|---|---|
| | | Nip1 | | Nip2 | | Nip3 | |
| | | X-gal | ONPG | X-gal | ONPG | X-gal | ONPG |
| wt | + | B | 1 | B | 1 | B | 1 |
| 14-5 | (+) | B | 0.61 | B | 0.55 | LB | 0.16 |
| 29-0 | + | B | 0.33 | B | 0.32 | B | 0.19 |
| 50-1 | − | W | <0.01 | W | 0.09 | W | 0.01 |
| 75-6 | + | B | 1.72 | B | 1.60 | B | 0.22 |
| 90-6 | − | W | <0.01 | W | 0.04 | W | 0.01 |
| 123-4 | − | W | 0.05 | LB | 0.24 | LB | 0.10 |
| 146-E | + | B | 0.87 | B | 0.98 | B | 0.28 |

The protein interaction studies were carried out in yeast strain GGY1::171.
Results of X-gal staining are indicated as B, blue; W, white; or LB, light blue.
[@]Results on suppression of cell death are based on Subramanian et al. (1993).
(+) Indicates positive at reduced levels.
β-galactosidase activities were determined from 3 to 4 independent colonies selected at random and grown in liquid selective SD medium (Rose et al., 1990). The β-galactosidase activity is expressed in units described by Rose et al., 1990.

All three 19 kD-interacting proteins were negative for interaction with mutants 50-1 (amino acids 50–51) (SEQ ID NO:11) and 90-6 (amino acids 90–96) (SEQ ID NO:13). Nip1 and Nip2 interacted at a reduced level with mutant 123-4 (substitutions for residues 123–124) (SEQ ID NO:14), but interacted more efficiently with the 19K mutant 75-6 (which carries a substitution for residues 75–76) (SEQ ID NO:12) than with wild-type (wt) 19K (SEQ ID NO:8).

Nip3 also exhibited a similar pattern of interaction; however, the overall level of expression of lacZ was lower. The studies identify two critical regions of the 19 kD protein marked by mutants 50-1 (SEQ ID NO:11) and 90-6 (SEQ ID NO:13) required for interaction with the cellular apoptosis-reducing proteins. In addition, sequences around residues 123–124 (mutant 123-4) (SEQ ID NO:14) also may influence the interactions.

The pattern of interaction of the three cellular proteins with the 19 kD protein is diagrammatically illustrated in FIG. 1. All the 19K mutants used make stable proteins in mammalian cells (Subramanian et al., 1993) and in yeast as GAL-4(1–147)-19 kD fusion proteins. Thus, the 19K mutants 50-1 (SEQ ID NO:11) and 90-6 (SEQ ID NO:13) defective for suppression of cell death, also are defective for interaction with the cellular proteins. The interaction of the cellular proteins with mutant 123-4 (SEQ ID NO:14) which also is defective in suppression of cell death is, in general, much reduced.

EXAMPLE 7

Since Bcl-2 functionally can substitute for 19K during adenovirus replication, the 19 kD-interacting cellular proteins also were shown to interact with the Bcl-2 protein.

The two hybrid analysis using a pMA424-based bait expressing the human Bcl-2 protein (Hockenbery et al., 1990) was used. Plasmids pMA-Bcl2 and pAS-Bcl2 express residues 1–239 of Bcl2. Yeast cells (GGY1::171) were transformed either with the pMA424-19K bait or with the pMA424-Bcl-2 bait along with each of the activation domain-tagged cDNA clones. The expression of lacZ was determined by the X-gal filter assay as well as by the liquid ONPG β-galactosidase assay (Table 4).

TABLE 4

Interaction of 19 kD-interacting proteins with Bcl-2

| | Relative level of lacZ expression[@] | | | |
|---|---|---|---|---|
| | 19 kD | | Bcl-2 | |
| Protein | X-gal | ONPG | X-gal | ONPG |
| Nip1 | B | 1 | B | 1.8 |
| Nip2 | B | 1 | B | 0.7 |
| Nip3 | B | 1 | B | 1.5 |

[@]Relative interaction is based on the β-galactosidase activity expressed in cells expressing the respective tagged cDNA clones and the 19K bait.
B, blue.

All three clones interacted with the Bcl-2 bait. Nip1 and Nip3 in general interacted more efficiently with the Bcl-2 bait as compared with the 19 kD bait. The interaction of Nip2 was slightly lower with Bcl-2 than with 19 kD.

Proteins coded by the three cDNA clones were prepared by in vitro transcription and translation according to protocols supplied by commercial vendors and incubated with cell extracts prepared from CHO cells or CHO cells infected with an adenovirus recombinant that overexpresses the human Bcl-2 protein (Ad-Bcl2) (obtained and available from T. Subramanian and B. Tarodi, St. Louis University Medical Center, St. Louis, Mo.). The proteins were immunoprecipitated with a hamster monoclonal antibody specific for human Bcl-2 (Hockenbery et al., 1990) and analyzed by SDS-PAGE.

All three 19 kD-interacting proteins could be precipitated from extracts prepared from cells infected with the Ad-Bcl2 virus while in contrast there was no significant amount of proteins precipitated from uninfected cells.

To further substantiate the interaction of the Nip proteins with Bcl-2, BSC40 cells infected with vTF7-3 (Fuerst et al., 1986) expressing the T7 RNA polymerase gene and cotransfected with plasmids expressing Bcl-2 and one of the HA-tagged Nip proteins were labeled, lysed and analyzed essentially as described in Example 4 for the 19 kD protein. Comparable levels of Bcl-2 protein were present in each sample as determined by immunoprecipitation using the Bcl-2 monoclonal antibody 6C8 (Hockenbery et al., 1990). Each sample was subjected to immunoprecipitation using the HA monoclonal antibody 12CA5 (Boehringer-Mannheim); the precipitated proteins were separated by SDS-PAGE, blotted and probed for the presence of Bcl-2. Bcl-2 clearly was coprecipitated with HA-Nip1, HA-Nip2 and HA-Nip3.

An alternate experiment in which the cells were cotransfected with each of the Nip proteins and either Bcl-2 or the vector plasmid and cell lysates were immunoprecipitated with antibody directed against the Bcl-2 protein and probed with anti-HA antibody, yielded comparable results for Nip1 and Nip3 (Nip2 is not transfered to nitrocellulose under standard blotting conditions) and provides additional support for the specificity of the interactions. Thus, using in vivo coimmunoprecipitation, a specific interaction between each of the Nip proteins and Bcl-2 was found. The results, together with the in vitro immunoprecipitation data, indicate that the three Nip proteins interact with Bcl-2 as well as with the 19 kD proteins.

Using bcl-2 as the bait in the two hybrid analysis, three additional regulating proteins (Bip for bcl-2 interacting protein) were identified. Two of the clones (Bip 1A, SEQ ID NOS:26–27 and Bip 13, SEQ ID NOS:30–31) also interact with the 19K bait, while clone Bip 5, SEQ ID NOS:28–29, did not. Bip 1A was tested for interaction with the 19K mutants as described in Example 5 and exhibited a similar pattern of interaction to that seen with NIP's 1, 2 and 3. Interaction was negative with mutant 90-6 (SEQ ID NO:13) and greatly diminished with mutant 50-1 (SEQ ID NO:11), as illustrated in FIG. 1.

EXAMPLE 8

The observation that the various 19 kD-interacting proteins also interact with the Bcl-2 protein is significant since the primary amino acid sequence of the 19 kD protein is not significantly homologous to Bcl-2 and related proteins (reviewed by Williams and Smith, 1993). Since four cellular proteins tested (Nip1, Nip2, Nip3 and Bip1A) failed to interact with 19K mutants 50-1 (SEQ ID NO:11) and 90-6 (SEQ ID NO:13), regions of homology corresponding to the mutated regions of 19 kD protein must exist. Three regions of homology between the amino acid sequences encompassing the 19K mutants (50-1 and 90-6) and Bcl-2 were identified.

Based thereon, three different deletion mutants within the Bcl-2 (SEQ ID NO:16) coding region where constructed by oligonucleotide-directed mutagenesis using commerically available kits (Amersham) (Table 2). The mutants lack Bcl-2 (SEQ ID NO:16) residues 42 to 48 (#42-8) (SEQ ID NO:17), 80 to 86 (#80-6) (SEQ ID NO:18) and 106 to 115 (#106-5) (SEQ ID NO:19) of Bcl-2. The mutants were cloned in pMA424 and used in the two hybrid assay. Interaction was determined by the lacZ expression assays (Table 5).

TABLE 5

Interaction of 19 kD-interacting proteins with Bcl-2 mutants

| | Relative level of lacZ expression[@] | | | | | |
|---|---|---|---|---|---|---|
| | Nip1 | | Nip2 | | Nip3 | |
| Mutant | X-gal | ONPG | X-gal | ONPG | X-gal | ONPG |
| wt | B | 1.0 | B | 1.0 | B | 1.0 |
| 42-8 | W | 0.16 | W | 0.09 | W | 0.19 |
| 80-6 | B | 1.21 | B | 0.80 | B | 2.87 |
| 106-5 | w | 0.01 | W | 0.06 | W | 0.11 |

[@]Relative interaction is based on the β-galactosidase activity expressed in cells expressing the respective tagged cDNA clones and the Bcl-2 baits expressing the various mutants.
B, blue; W, white.

Mutants 42-8 and 106-5 were defective for interaction with the three clones tested while mutant 80-6 was not. Since the amino acid sequences of Bcl-2 deleted in mutants 42-8 and 106-5 appear to be homologous to sequences around 19K mutants 90-6 and 50-1, respectively, the 19 kD-interacting proteins recognize bipartite sequence motifs common to both the 19 kD and Bcl-2 proteins (FIG. 1).

EXAMPLE 9

The DNA sequences of the six cDNA clones were determined by dideoxy sequencing using the Sequenase kit (U.S. Biochemicals) of pAct-based plasmids (Durfee et al., 1993) or after subcloning into the pBluescript II KS(+) vector (Stratagene, San Diego, Calif.) using Sequenase version 2 (U.S. Biochemical Corp.). Sequencing first was initiated with primers complementary to sequences upstream of the cDNA cloning site in pAct or the T3 promoter of pBluescript. Subsequently, other primers were synthesized on the basis of newly determined sequences and used for sequencing both strands. The reading frame in relation to the GAL4 activation domain was established.

Since the activation domain is tagged at the 5' end of the cDNA's, a fraction of cDNA's isolated by the two hybrid system may be lacking the sequences corresponding to native 5' ends of the various mRNA's. Hence, the 5'-upstream sequences corresponding to the three isolated cDNA clones were obtained by reverse transcription of poly(A)-containing RNA prepared from human HeLa cells or from human placenta and PCR amplification (Frohman et al., 1988) using two nested primers (5'RACE) using a commercially available kit (5'AmpliFINDER, Clonetech) or from cDNA clones isolated from a human B cell cDNA library (Ausubel et al., 1992).

Downstream sequences were obtained by 3'RACE (described hereinbelow) using a commercially available kit (GibcoBRL). The Bluescript-based cDNA clones were prepared after infection with the helper phage and sequenced using appropriate primers. The DNA fragments obtained by RACE were cloned and sequenced.

The RACE analysis provided additional DNA sequences corresponding to three codons including an ATG codon for clone 22 (Nip1) while extensive analysis did not provide additional protein coding sequences corresponding to cDNA clones 44 (Nip2) and 91 (Nip3). The coding region of clone 44 at the 3' end (30 amino acids) was obtained by 3' RACE analysis.

For Bip5, 139 bp of 5' sequences were obtained as follows. The two hybrid clone contained nucleotides 109 to 1542. Comparison of the Bip5 sequence with a human fetal brain cDNA clone revealed substantial sequence identity and overlap (clone T08302, EST 06193, Adams et al., 1993) between the two clones. Clone T08302 contains a 366 bp fragment and includes an open reading frame beginning at the ATG of the clone. T08302 was ligated to the 5' end of the Bip5 clone following PCR amplification.

EXAMPLE 10

The amino acid sequences of Nip1 (SEQ ID NO:21), Nip2 (SEQ ID NO:23), Nip3 (SEQ ID NO:25), Bip1A (SEQ ID NO:27), Bip5 (SEQ ID NO:29) and Bip13 (SEQ ID NO:31) based on DNA sequences are presented in Table 6. Putative transmembrane domains of Nip1 and Nip3 are underlined.

The amino acid sequences were analyzed to determine if any similarity to other sequences existed in various known and available data banks (GenBank, PIR and SwissProt National Center for Biotechnology Information (NCBI) using the FASTA, TFASTA programs (Pearson & Lipman 1988) available in the University of Wisconsin Genetic Computer group (UWGCG package) and BLAST (NCBI) (Alschul et al., 1990) algorithms. The sequences also were analyzed by the PROSITE (UWGCG Software package) program to identify functional sequence motifs.

Nip1(SEQ ID NO:21) is a 228 amino acid protein and contains a putative membrane-spanning hydrophobic domain. The presence of the membrane-spanning domain enables the protein to form stable associations with cellular membranes and accounts for the observed localization of the protein to the nuclear envelope/endoplasmic reticulum region of the cell.

Sequence comparison of Nip1(SEQ ID NO:21) indicated that the protein is not significantly homologous to other known proteins. However, a 59 to 83 amino acid region of Nip1 has homology (29 to 36 per cent identity and 55 to 60 per cent similarity) to a conserved region (FIG. 2A) within the catalytic domain of three mammalian (rat, mouse and cow) calmodulin-dependent 3'-5'-cyclic nucleotide phosphodiesterases (PDE) (SEQ ID NO:34) (Bentley et al., 1992; Polli et al., 1992; Repaske et al., 1992).

Because Nip1 is likely to possess an enzymatic activity, Nip1 can be used as a diagnostic tool to ascertain the state of the cell. Hence, excess of reduced Nip1 phosphodiesterase activity can be a means for monitoring the metabolic state of a cell, tissue or organ.

Nip2 (SEQ ID NO:23) is a 314 amino acid protein. Sequence comparison revealed that a 126 amino acid region of Nip2 shares significant homology (47 per cent identity and 66 per cent similarity; FIG. 2C) to the human GTPase activating protein RhoGAP (SEQ ID NO:35) (Barfod et al., 1993; Lancaster et al., 1994). The homology between Nip2 and RhoGAP does not extend to the functional domain of RhoGAP and is located in an upstream region which has been postulated to be removed by proteolysis (Barfod et al., 1993).

A scrutiny of the Nip2 sequence also revealed the presence of a putative $Ca^{++}$—binding motif (amino acids 79–90 of SEQ ID NO:23) (FIG. 2B).

Even though Nip2 does not contain a membrane-spanning hydrophobic domain, indirect immunofluorescence analysis indicates that it is associated with cytoplasmic structures.

Nip3 (SEQ ID NO:25) is a 194 amino acid protein and contains a presumptive membrane-spanning hydrophobic domain. Nip3 also appears to be a novel protein. However, the cDNA sequence is highly homologous to a rat cDNA clone which encodes the rat brain calbindin-D protein (Hunziker and Schrickel, 1988). A smaller cDNA clone isolated from human fetal brain (Adams et al., 1992) is identical to sequences within the Nip3 coding region. cDNA clone 91 (Nip3) and the fetal brain cDNA do not contain the coding sequences for calbindin. Similarly, two other cDNA clones containing Nip3 sequences isolated from a human B cell cDNA library do not contain the calbindin coding sequences. An extensive search for additional sequences in DNA amplified by 5'RACE of human placental RNA with primers specific for clone 91 did not yield additional 5' sequences corresponding to calbindin coding sequences.

Thus, Nip3 is coded by a unique mRNA in human cells. That notion is in agreement with the observation that rat calbindin cDNA hybridizes to multiple mRNA species from human membrane (Iacopino and Christakos, 1990).

All three cellular proteins contain sequence motifs designated PEST (enriched in proline, glutamic acid, serine and threonine) (SEQ ID NO:33) sequences (Rogers et al, 1986) suggesting that the proteins may be degraded rapidly and expressed in a stage-specific manner (Rogers et al., 1986).

Bip1A (SEQ ID NO:27) is a 160 amino acid protein.

Bip5 (SEQ ID NO:29) is a 259 amino acid protein and does not exhibit significant homology to other known proteins.

On sequencing, it was determined that clone Bip13 (SEQ ID NO:31) bears a high degree of homology with CD22 (Wilson et al., 1991; Stamenkovic and Seed, 1990). CD22 is known to increase intracellular calcium and may be a B cell activator, however, the role of CD22 in apoptosis heretofore was unknown.

TABLE 6

Amino Acid and Nucleic Acid Sequences

A. Nip1

```
AGTCCCCAACATGGCGGCTCCCCAAGACGTCCACGTCCGGATCTGTAACCAAGAGATTGT
          M  A  A  P  Q  D  V  H  V  R  I  C  N  Q  E  I  V

CAAATTTGACCTGGAGGTGAAGGCGCTTATTCAGGATATCCGTGATTGTTCAGGACCCTT
 K  F  D  L  E  V  K  A  L  I  Q  D  I  R  D  C  S  G  P  L

AAGTGCTCTTACTGAACTGAATACTAAAGTAAAAGAGAAATTTCAACAGTTGCGTCACAG
 S  A  L  T  E  L  N  T  K  V  K  E  F  Q  Q  L  R  H  R

AATACAGGACCTGGAGCAGTTGGCTAAAGAGCAAGACAAAGAATCAGAGAAACAACTTCT
 I  Q  D  L  E  Q  L  A  K  E  Q  D  K  E  S  E  K  Q  L  L

ACTCCAGGAAGTGGAGAATCACAAAAAGCAGATGCTCAGCAATCAGGCCTCATGGAGGAA
 L  Q  E  V  E  N  H  K  K  Q  M  L  S  N  Q  A  S  W  R  K

AGCTAATCTCACCTGCAAAATTGCAATCGACAATCTAGAGAAAGCAGAACTTCTTCAGGG
 A  N  L  T  C  K  I  A  I  D  N  L  E  K  A  E  L  L  Q  G

AGGAGATCTCTTAAGGCAAAGGAAAACCACCAAAGAGAGCCTGGCCCAGACATCCAGTAC
 G  D  L  L  R  Q  R  K  T  T  K  E  S  L  A  Q  T  S  S  T

CATCACTGAGAGCCTCATGGGGATCAGCAGGATGATGGCCCAGCAGGTCCAGCAGAGCGA
 I  T  E  S  L  M  G  I  S  R  M  M  A  Q  Q  V  Q  Q  S  E

GGAGGCCATGCAGTCTCTAGTCACTTCTTCACGAACGATCCTGGATGCAAATGAAGAATT
 E  A  M  Q  S  L  V  T  S  S  R  T  I  L  D  A  N  E  E  F

TAAGTCCATGTCGGCACCATCCAGCTGGGCCGGAAGCTTATCACAAAATACAATCGCCG
 K  S  M  S  G  T  I  Q  L  G  R  K  L  I  T  K  Y  N  R  R

GGAGCTGACGGACAAGCTTCTCATCTTCCTTGCGCTACGCCTGTTTCTTGCTACGGTCCT
 E  L  T  D  K  L  L  I  F  L  A  L  R  L  F  L  A  T  V  L

CTATATTGTGAAAAAGCGGCTCTTTCCATTTTTGTGAGATCCCAAAGGTGCCAGTTCTGG
 Y  I  V  K  K  R  L  F  P  F  L

CCCTTTCAGCTCCTGTTTCAGGATCTGTCCTGGTTCCTGAGCTCTAGGCTGCTAAGCTGA
GCCACACACCCCTCCGTTTTGCACCAGTTGCCTGCAGGTTGGATGGAACACAGTGCCCCA
CTTTTCTGCAAGTAGCTGGCTTGTAAAGGGTGAACAGAGCCATGGGAGGAAGGTCTGGCA
TTGGGATGCCGCCCTGGGGACATACGAACCGCCTCCTTCCACCATTGTGCACTATGGGAG
GCCGCTGCTGCGTGGAGCACTTAAAGTCCAGCCTCCAGGACCGGATGCCCCTCCTGTCTC
CCGCTCCCATCGTGCCCTTAAATGCCAGATCTGGTGGAGGGAAGAGAGAAGAGGTAGGAA
GAAAGGTGATGAAAACTCCTG
```

B. Nip2

```
                   CTGCGGCCGGGGGATTGGGCCGGGGTATCCACCGCCGACCGAG
GGGAGCGGCGTCCGCTCGGCCCTGCTTTTTGCGACCTGCCGTCAGCCCCACGTCGCCGGC
CTGGAGGGGCGAAGAGGACGAGGGGCGACGAAGGCCCAAGGCTTCCTCCGGGGACATTGG
CTCCCTGGATTATCAAGCAGTTTGTAGTTGACATTGAATCCAGGCTGAGGATGGAAGGTG
                                                      M  E  G

TGGAACTTAAAGAAGAATGGCAAGATGAAGATTTTCCGATACCTTTACCAGAAGATGATA
 V  E  L  K  E  E  W  Q  D  E  D  F  P  I  P  L  P  E  D  D

GTATTGAAGCAGATATACTAGCTATAACTGGACCAGAGGACCAGCCTGGCTCACTAGAAG
 S  I  E  A  D  I  L  A  I  T  G  P  E  D  Q  P  G  S  L  E

TTAATGGAAATAAAGTGAGAAAGAAACTAATGGCTCCAGACATTAGCCTGACACTGGATC
 V  N  G  N  K  V  R  K  K  L  M  A  P  D  I  S  L  T  L  D

CTAGTGATGGCTCTGTATTGTCAGATGATTTGGATGAAAGTGGGGAGATTGACTTAGATG
 P  S  D  G  S  V  L  S  D  D  L  D  E  S  G  E  I  D  L  D

GCTTAGACACACCGTCAGAGAATAGTAATGAGTTTGAGTGGGAAGATGATCTTCCAAAAC
 G  L  D  T  P  S  E  N  S  N  E  F  E  W  E  D  D  L  P  K

CCAAGACTACTGAAGTAATTAGGAAAGGCTCAATTACTGAATACACAGCAGCAGAGGAAA
 P  K  T  T  E  V  I  R  K  G  S  I  T  E  Y  T  A  A  E  E

AAGAAGATGGACGACGCTGGCGTATGTTCAGGATTGGAGAACAGGACCACAGGGTTGATA
 K  E  D  G  R  R  W  R  M  F  R  I  G  E  Q  D  H  R  V  D

TGAAGGCAATTGAACCCTATAAAAAAGTTATCAGCCATGGGGGATATTATGGGGATGGAT
 M  K  A  I  E  P  Y  K  K  V  I  S  H  G  G  Y  Y  G  D  G
```

TABLE 6-continued

Amino Acid and Nucliec Acid Sequences

```
TAAATGCCATTGTTGTATTTGCTGTCTGTTTCATGCCTGAAAGTAGTCAGCCTAACTATA
 L  N  A  I  V  V  F  A  V  C  F  M  P  E  S  S  Q  P  N  Y

GATACCTGATGGACAATCTTTTTAAATATGTTATTGGCACTTTGGAGCTATTAGTAGCAG
 R  Y  L  M  D  N  L  F  K  Y  V  I  G  T  L  E  L  L  V  A

AAAACTACATGATAGTTTATTTAAATGGTGCAACAACTCGAAGAAAAATGCCCAGTCTGG
 E  N  Y  M  I  V  Y  L  N  G  A  T  T  R  R  K  M  P  S  L

GATGGCTCAGGAAATGTTATCAGCAAATTGATAGAAGGTTACGGAAAAATCTAAAATCCC
 G  W  L  R  K  C  Y  Q  Q  I  D  R  R  L  R  K  N  L  K  S

TAATCATTGTACATCCTTCTTGGTTTATCAGAACACTTCTGGCTGTTACAAGACCATTTA
 L  I  I  V  H  P  S  W  F  I  R  T  L  L  A  V  T  R  P  F

TTAGCTCGAAATTCAGCCAAAAAATTAGATACGTGTTTAATTTGGCAGAACTAGCAGAAC
 I  S  S  K  F  S  Q  K  I  R  Y  V  F  N  L  A  E  L  A  E

TTGTCCCCATGGAATACGTTGGCATACCAGAATGCATAAAACAAGTTGATCAAGAACTTA
 L  V  P  M  E  Y  V  G  I  P  E  C  I  K  Q  V  D  Q  E  L

ATGGAAAACAAGATGAACCGAAAAATGAACAGTAAGTTTGGCATCTAGTCCAAACAAGAC
 N  G  K  Q  D  E  P  K  N  E  Q

TGAAGAATGTGCTGATGGAGCAGTGCTGTTTCTGCATTCATAATGCATTTATTGGCCAT
ATTTTTATGTAACCTGTTACAAAATAGACTTGACTTTTTCATAATGGACTTTTGTATTATAC
AAGGGACTGTTCACTGCTGTACTGGTTTGCAAATTTCTTGAATTTAGCTCTTTATGCTAACT
GTATTATTATCATTTTATAT
```

C. Nip3

```
AAAGAGATCTGGAATTCGGATCCTCGAGGCCACGAAGGCCACCGCCCGCAGCTGAAGCAC
ATCCGCAGCCCGGCGCGACTCCGATCGCCGCAGTTGCCCTCTGGCGCCATGTCCGAGAAC
                                                  M  S  E  N

GGAGCGCCCGGGATGCAGGAGGAGAGCCTGCAGGGCTCCTGGGTAGAACTGCACTTCAGC
 G  A  P  G  M  Q  E  E  S  L  Q  G  S  W  V  E  L  H  F  S

AATAATGGGAACGGGGGCAGCGTTCCAGCCTCGGTTTCTATTTATAATGGAGACATGGAA
 N  N  G  N  G  G  S  V  P  A  S  V  S  I  Y  N  G  D  M  E

AAAATACTGCTGGACGCACAGCATGAGTCTGGACGGAGTAGCTCCAAGAGCTCTCACTGT
 K  I  L  L  D  A  Q  H  E  S  G  R  S  S  K  S  S  H  C

GACAGCCCACCTCGCTCGCAGACACCACAAGATACCAACAGGGCTTCTGAAACAGATACC
 D  S  P  P  R  S  Q  T  P  Q  D  T  N  R  A  S  E  T  D  T

CATAGCATTGGAGAGAAAAACAGCTCACAGTCTGAGGAAGATGATATTGAAAGAAGGAAA
 H  S  I  G  E  K  N  S  S  Q  S  E  E  D  D  I  E  R  R  K

GAAGTTGAAAGCATCTTGAAGAAAAACTCAGATTGGATATGGGATTGGTCAAGTCGGCCG
 E  V  E  S  I  L  K  K  N  S  D  W  I  W  D  W  S  S  R  P

GAAAATATTCCCCCCAAGGAGTTCCTCTTTAAACACCCGAAGCGCACGGCCACCCTCAGC
 E  N  I  P  P  K  E  F  L  F  K  H  P  K  R  T  A  L  S

ATGAGGAACACGAGCGTCATGAAGAAAGGGGGCATATTCTCTGCAGAATTTCTGAAAGTT
 M  R  N  T  S  V  M  K  K  G  G  I  F  S  A  E  F  L  K  V

TTCCTTCCATCTCTGCTGCTCTCTCATTTGCTGGCCATCGGATTGGGGATCTATATTGGA
 F  L  P  S  L  L  L  S  H  L  L  A  I  G  L  G  I  Y  I  G

AGGCGTCTGACAACCTCCACCAGCACCTTTTGATGAAGAACTGGAGTCTGACTTGGTTCG
 R  R  L  T  T  S  T  S  T  F

TTAGTGGATTACTTCTGAGCTTGCAACATAGCTCACTGAAGAGCTGTTAGATCCTGGGCC
TTCGTGGCTCGAGAGACTAGAATCGCAGATACGAAAACCCCGCAGC
```

D. Bip1A

```
                              CAGCATCGCCGCCGCCAGAGGAGAAATGTCTGAAGTA
                                                       M  S  E  V

AGACCCCTCTCCAGAGACATCTTGATGGAGACCCTCCTGTATGAGCAGCTCCTGGAACCC
 R  P  L  S  R  D  I  L  M  E  T  L  L  Y  E  Q  L  L  E  P
```

TABLE 6-continued

Amino Acid and Nucliec Acid Sequences

CCGACCATGGAGGTTCTTGGCATGACTGACTCTGAAGAGGACCTGGACCCTATGGAGGAC
P   T   M   E   V   L   G   M   T   D   S   E   E   D   L   D   P   M   E   D

TTCGATTCTTTGGAATGCATGGAGGGCAGTGACGCATTGGCCCTGCGGCTGGCCTGCATC
F   D   S   L   E   C   M   E   G   S   D   A   L   A   L   R   L   A   C   I

GGGGACGAGATGGACGTGAGCCTCAGGGCCCCGCGCCTGGCCCAGCTCTCCGAGGTGGCC
G   D   E   M   D   V   S   L   R   A   P   R   L   A   Q   L   S   E   V   A

ATGCACAGCCTGGGTCTGGCTTTCATCTACGACCAGACTGAGGACATCAGGGATGTTCTT
M   H   S   L   G   L   A   F   I   Y   D   Q   T   E   D   I   R   D   V   L

AGAAGTTTCATGGACGGTTTCACCACACTTAAGGAGAACATAATGAGGTTCTGGAGATCC
R   S   F   M   D   G   F   T   T   L   K   E   N   I   M   R   F   W   R   S

CCGAACCCCGGGTCCTGGGTGTCCTGCGAACAGGTGCTGCTGGCGCTGCTGCTGCTGCTG
P   N   P   G   S   W   V   S   C   E   Q   V   L   L   A   L   L   L   L   L

GCGCTGCTGCTGCCGCTGCTCAGCGGGGGCCTGCACCTGCTGCTCAAGTGAGGCCCCGGC
A   L   L   L   P   L   L   S   G   G   L   H   L   L   L   K

GGCTCAGGGCGTGGCTGGCCCCACCCCCATGACCACTGCCCTGGAGGTGGCGGCCTGCTGCT
GTTATCTTTTTAACTGTTTTCTCATGATGCCTTTTTATATTTAAACCCCGAGATAGTG
CTGGAACACTGCTGAGGTTTTATACTCAGGTTTTTTGTTTTTTTTTTATTCCAGTTTTCG
TTTTTTCTAAAAGATGAATTCCTATGGCTCTGCAATTGTCACCGGTTAACTGTGGCCTGT
GCCCAGGAAGAGCCATTCACTCCTGCCCCTGCCCACACGGCAGGTAGCAGGGGAGTGCT
GGTCACACCCCTGTGTGATATGTGATGCCCTCGGCAAAGAATCTACTGGAATAGATTCCG
AGGAGCAGGAGTGCTCAATAAAATGTTGGTTTCCAGCAAAAAAAAAAAAAAAGGCCTTCGT
GGCCTCGAG

E. Bip5

ATG GAC GCC TGG GTC CGC TTC AGT GCT CAG AGC CAA GCC CGG
 M   D   A   W   V   R   F   S   A   Q   S   Q   A   R

GAG CGG CTG TGT AGG GCC GCC CAG TAT GCT TGC TCT CTT CTT GGC
 E   R   L   C   R   A   A   Q   Y   A   C   S   L   L   G

CAT GCG CTG CAG AGG CAT GGA GCC AGT CCT GAG TTA CAG AAA CAG
 H   A   L   Q   R   H   G   A   S   P   E   L   Q   K   Q

ATT CGA CAA CTG GAG AGC CAC CTG AGC CTT GGA AGA AAG CTT CTA
 I   R   Q   L   E   S   H   L   S   L   G   R   K   L   L

CGC CTG GGT AAC TCA GCA GAT GCC CTT GAG TCA GCC AAA AGA GCT
 R   L   G   N   S   A   D   A   L   E   S   A   K   R   A

GTT CAC CTA TCA GAT GTT GTC CTG AGA TTC TGC ATC ACT GTT AGT
 V   H   L   S   D   V   V   L   R   F   C   I   T   V   S

CAC CTC AAT CGA GCC TTG TAC TTC GCC TGT CAC AAT GTC CTG TGG
 H   L   N   R   A   L   Y   F   A   C   H   N   V   L   W

GCT GGA AAG TCT GGA CTG GCT CCC CGT GTG GAT CAG GAG AAG TGG
 A   G   K   S   G   L   A   P   R   V   D   Q   E   K   W

GCC CAG CGT TCA TTC AGG TAC TAT TTG TTT TCC CTC ATC ATG AAT
 A   Q   R   S   F   R   Y   Y   L   F   S   L   I   M   N

TTG AGC CGT GAT GCT TAT GAG ATT CGC CTA CTG ATG GAG CAA GAG
 L   S   R   D   A   Y   E   I   R   L   L   M   E   Q   E

TCT TCT GCT TGT AGC CGG CGA CTG AAA GGT TCT GGA GGA GGA GTC
 S   S   A   C   S   R   R   L   K   G   S   G   G   G   V

CCA GGA GGA AGT GAA ACT GGG GGA CTT GGG GGA CCA GGG ACT CCA
 P   G   G   S   E   T   G   G   L   G   G   P   G   T   P

GGA GGA GGT CTG CCC CAA CTG GCT CTG AAA CTT CGG CTG CAA GTC
 G   G   G   L   P   Q   L   A   L   K   L   R   L   Q   V

CTG CTC CTG GCT CGA GTC CTT AGA GGT CAT CCC CCA CTT CTG CTA
 L   L   L   A   R   V   L   R   G   H   P   P   L   L   L

GAC GTG GTC AGA AAT GCC TGT GAT CTC TTC ATT CCT CTG GAC AAA
 D   V   V   R   N   A   C   D   L   F   I   P   L   D   K

CTA GCG CTC TGG CGC TGT GGC CCT GGG ATT GTG GGG CTT TGT GGC
 L   A   L   W   R   C   G   P   G   I   V   G   L   C   G

TABLE 6-continued

Amino Acid and Nucliec Acid Sequences

```
CTC GTG TCC TCC ATC CTG TCT ATT CTC ACC CTA ATC TAT CCC TGG
 L   V   S   S   I   L   S   I   L   T   L   I   Y   P   W

CTA CGA CTC AAG CCC TGA CTT CCG GTA CAG GAT AAG GAG GGG ACC
 L   R   L   K   P

TGA ATT GGT GAG ATG GAA TCT TAG ATC GTC CCC ATG TGC CAG CCT
CAT TCG AAT TCT ACT CTT TGG TTA AAG TTA GAA ATT CAG AGA TTT
AGG GGT GGA GGA GGA AGA GCT TTG GGG AAG ATG AGG TAA GGA AAG
ATG ACT CGT GAA GTT AAT AGG ATG TCT CTA ATT TCT AGA
```

F. Bip13

```
                        AGTCAAGTCGAGTTTCTTTCTTTGCATGTCACTGGCCAATCCTCTT
                         S  Q  V  E  F  L  C  M  S  L  A  N  P  L
CCAACAAATTACACGTGGTACCACAATGGGAAAGAAATGCAGGGAAGGACAGAGGAGAAA
 P  T  N  Y  T  W  Y  H  N  G  K  E  M  Q  G  R  T  E  E  K
GTCCACATCCCAAAGATCCTCCCCTGGCACGCTGGGACTTATTCCTGTGTGGCAGAAAAC
 V  H  I  P  K  I  L  P  W  H  A  G  T  Y  S  C  V  A  E  N
ATTCTTGGTACTGGACAGAGGGGCCCGGGAGCTGAGCTGGATGTCCAGTATCCTCCCAAG
 I  L  G  T  G  Q  R  G  P  G  A  E  L  D  V  Q  Y  P  P  K
AAGGTGACCACAGTGATTCAAAACCCCATGCCGATTCGAGAAGGAGACACAGTGACCCTT
 K  V  T  T  V  I  Q  N  P  M  P  I  R  E  G  D  T  V  T  L
TCCTGTAACTACAATTCCAGTAACCCCAGTGTTACCCGGTATGAATGGAAACCCCATGGC
 S  C  N  Y  N  S  S  N  P  S  V  T  R  Y  E  W  K  P  H  G
GCCTGGGAGGAGCCATCGCTTGGGGTGCTGAAGATCCAAAACGTTGGCTGGGACAACACA
 A  W  E  E  P  S  L  G  V  L  K  I  Q  N  V  G  W  D  N  T
ACCATCGCCTGCGCACGTTGTAATAGTTGGTGCTCGTGGGCCTCCCCTGTCGCCCTGAAT
 T  I  A  C  A  R  C  N  S  W  C  S  W  A  S  P  V  A  L  N
GTCCAGTATGCCCCCCGAGACGTGAGGGTCCGGAAAATCAAGCCCCTTTCCGAGATTCAC
 V  Q  Y  A  P  R  D  V  R  V  R  K  I  K  P  L  S  E  I  H
TCTGGAAACTCGGTCAGCCTCCAATGTGACTTCTCAAGCAGCCACCCCAAAGAAGTCCAG
 S  G  N  S  V  S  L  Q  C  D  F  S  S  H  P  K  E  V  Q
TTCTTCTGGGAGAAAAATGGCAGGCTTCTGGGGAAAGAAAGCCAGCTGAATTTTGACTCC
 F  F  W  E  K  N  G  R  L  L  G  K  E  S  Q  L  N  F  D  S
ATCTCCCCAGAAGATGCTGGGAGTTACAGCTGCTGGGTGAACAACTCCATAGGACAGACA
 I  S  P  E  D  A  G  S  Y  S  C  W  V  N  N  S  I  G  Q  T
GCGTCCAAGGCCTGGACACTTGAAGTGCTGTATGCACCCAGGAGGCTGCGTGTGTCCATG
 A  S  K  A  W  T  L  E  V  L  Y  A  P  R  R  L  R  V  S  M
AGCCCGGGGGACCAAGTGATGGAGGGGAAGAGTGCAACCCTGACCTGTGAGAGTGACGCC
 S  P  G  D  Q  V  M  E  G  K  S  A  T  L  T  C  E  S  D  A
AACCCTCCCGTCTCCCACTACACCTGGTTTGACTGGAATAACCAAAGCCTCCCCCACCAC
 N  P  P  V  S  H  Y  T  W  F  D  W  N  N  Q  S  L  P  H  H
AGCCAGAAGCTGAGATTGGAGCCGGTGAAGGTCCAGCACTCGGGTGCCTACTGGTGCCAG
 S  Q  K  L  R  L  E  P  V  K  V  Q  H  S  G  A  Y  W  C  Q
GGGACCAACAGTGTGGGCAAGGGCCGTTCGCCTCTCAGCACCCTTACTGTCTACTATAGC
 G  T  N  S  V  G  K  G  R  S  P  L  S  T  L  T  V  Y  Y  S
CCGGAGACCATCGGCAGGCGAGTGGCTGTGGGACTCGGGTCCTGCCTCGCCATCCTCATC
 P  E  T  I  G  R  R  V  A  V  G  L  G  S  C  L  A  I  L  I
CTGGCAATCTGTGGGCTCAAGCTCCAGCGACGTTGGAAGAGGACACAGAGCCAGCAGGGG
 L  A  I  C  G  L  K  L  Q  R  R  W  K  R  T  Q  S  Q  Q  G
CTTCAGGAGAATTCCAGCGGCCAGAGCTTCTTTGTGAGGAATAAAAAGGTTAGAAGGGCC
 L  Q  E  N  S  S  G  Q  S  F  F  V  R  N  K  K  V  R  R  A
CCCCTCTCTGAAGGCCCCCACTCCCTGGGATGCTACAATCCAATGATGGAAGATGGCATT
 P  L  S  E  G  P  H  S  L  G  C  Y  N  P  M  M  E  D  G  I
AGCTACACCACCCTGCGCTTTCCCGAGATGAACATACCACGAACTGGAGATGCAGAGTGG
 S  Y  T  T  L  R  F  P  E  M  N  I  P  R  T  G  D  A  E  S
```

TABLE 6-continued

Amino Acid and Nucliec Acid Sequences

```
TCAGAGATGCAGAGACCTCCCCGGACCTGCGATGACACGGTCACTTATTCAGCATTGCAC
 S   E   M   Q   R   P   P   R   T   C   D   D   T   V   T   Y   S   A   L   H

AAGCGCCAAGTGGGCGACTATGAGAACGTCATTCCAGATTTTCCAGAAGATGAGGGGATT
 K   R   Q   V   G   D   Y   E   N   V   I   P   D   F   P   E   D   E   G   I

CATTACTCAGAGCTGATCCAGTTTGGGGTCGGGGAGCGGCCTCAGGCACAAGAAAATGTG
 H   Y   S   E   L   I   Q   F   G   V   G   E   R   P   Q   A   Q   E   N   V

GACTATGTGATCCTCAAACATTGACACTGGATGGGCTGCAGCAGAGGCACTGGGGGCAGC
 D   Y   V   I   L   K   H

GGGGGCCAGGGAAGTCCCCGAGTTTCCCCAGACACCGCCACATGGCTTCCTCCTGCGTGC
ATGTGCGCACACACACACACACACGCACACACACACACACACTCACTGCGGAGAACCT
TGTGCCTGGCTCAGAGCCAGTCTTTTTGGTGAGGGTAACCCCAAACCTCCAAAACTCCTG
CCCCTGTTCTCTTCCACTCTCCTTGCTACCCAGAAATCATCTAAATACCTGCCCTGACAT
GCACACCTCCCCTGCCCCACCAGCCCACTGGCCATCTCCACCCGGAGCTGCTGTGTCCTC
TGGATCTGCTCGTCATTTTCCTTCCCTTCTCCATCTCTCTGGCCCTCTACCCCTGATCTG
ACATCCCCACTCACGAATATTATGCCCAGTTTCTGCCTCTGAGGGAAAGCCCAGAAAAGG
ACAGAAACGAAGTAGAAAGGGGCCCAGTCCTGGCCTGGCTTCTCCTTTGGAAGTGAGGCA
TTGCACGGGGAGACGTACGTATCAGCGGCCCCTTGACTCTGGGGACTCCGGGTTTGAGAT
GGACACACTGGTGTGGATTAACCTGCCAGGGAGACAGAGCTCACAATAAAAATGGCTCAG
ATGCCACTTCAAAGAAAAAAAAAA
```

EXAMPLE 11

The cellular apoptosis-regulating proteins also interact with the BHRF-1 protein of Epstein-Barr virus. BHRF-1 (Baer et al., 1984; Pearson et al., 1987) shares significant homology with the Bcl-2 protein (Cleary et al., 1986; Williams and Smith, 1993). The BHRF-1 protein can protect against cell death induced by certain apoptosis-inducing stimuli such as serum depletion and the DNA damaging agents (Henderson et al., 1993). Sequences homologous to the 19 kD motifs are present in the BHRF-1 protein. The two domains of the 19 kD and Bcl-2 proteins required for interaction with the cellular proteins are absent in Bax, a homolog of Bcl-2 (Oltvai et al., 1993). The absence of the two domains in Bax, which has a cell death promoting activity, supports the observation that the two domains are important for mediating cell survival by the 19 kD and Bcl-2 proteins.

The 19 kD protein of Ad2 and Ad5 contains a region (residues 60–69) (see Table 1) homologous to a conserved domain (termed domain I) present in various Bcl-2-related proteins, including Bax (Williams and Smith, 1993; Oltvai et al., 1993). Nip1, Nip2 and Nip3 do not interact with human Bax, which contains domain I, in the yeast two hybrid assay suggesting that the conserved domain I may not be essential for interaction of Nip1, Nip2 and Nip3. However, Bcl-2 can suppress cell death promoted by Bax, possibly by forming Bax-Bcl-2 heterodimers (Oltvai et al., 1993).

In the nematode C. elegans, apoptotic cell death is inhibited by a survival promoting gene designated ced-9 (Hengartner et al., 1992). The ced-9 gene antagonizes the activity of two nematode cell death-inducing genes, ced-3 and ced-4, which are activated during programmed cell death (Yuan and Horvitz, 1990). Bcl-2 can substitute functionally for ced-9 in C. elegans (Vaux et al., 1991).

The mammalian IL-1β-converting enzyme (ICE), a homolog of ced-3 (Yuan et al., 1993; Miura et al., 1993), induces cell death in mammalian cells. The activity of ICE can be suppressed by Bcl-2 (Miura et al., 1993) although it is not known whether there is any physical interaction between ICE and Bcl-2.

EXAMPLE 12

The homology between Nip2 and Rho GTPase-activating protein (RhoGAP) raises the possibility that the signal transduction pathway may play a key role in counteracting the cell death inducing stimuli. In this context, it has recently been reported that the Bcl-2 protein associates with R-ras (Fernandez-Sarabia & Bischoff, 1993), a member of Ras superfamily. Nip2 may modulate the activity of RhoGAP through alternate mechanisms such a formation of RhoGAP-Nip2 heterodimers. Because the homology between Nip2 and RhoGAP is located upstream of the N-terminus of active RhoGAP (Garrett et al., 1991), Nip2 might affect the activity of RhoGAP by interfering with the processing of RhoGAP.

Nip2 has a putative $Ca^{+2}$—binding motif. Since intracellular $Ca^{+2}$ appears to be an important mediator of apoptotic cell death, it is possible that the activity of Nip2 may be modulated by $Ca^{+2}$. Hence, interactions between the 19 Kd protein and Nip2 could remove the influence thereof on RhoGAP activity, thus affecting $p21^{rho}$ and potentially other members of the ras superfamily.

REFERENCES

Adams, et al., (1993), Nature Genetics, 4, 373–380
Alberts, B. et al., (1989), "Molecular biology of the cell", Garland Publishing, Inc., N.Y.
Alnemri, E. S., (1992a), Cancer Res. 52, 491–495
Alnemri, E. S. et al., (1992b), Proc. Natl. Acad. Sci. USA 89, 7295–7299
Adams, M. D. et al., (1992), Nature 355, 632–634
Altschul, S. F. et al., (1990), J. Mol. Biol. 215, 403–410
Ambrus, J., Jr. et al., (1993), Proc. Natl. Acad. Sci. USA 90, 6330–6334
Ausubel, F. M. et al., "Current Protocols in Molecular Biology", John Wiley & Sons, N.Y.
Baer, R. et al., (1984) Nature 310:207–211.
Baffy, G. et al., (1993), J. Biol. Chem. 268, 6511–6519
Barfod, E. T., (1993), J. Biol. Chem. 268, 26059–26062
Bartel, P., (1993), Biotechniques 14, 920–924
Bentley, J. K., (1992), J. Biol. Chem. 267, 18676–18682
Berridge, M. J., (1987), Annu. Rev. Biochem. 56, 159–193

Berridge, M. J. & Irvine, R. F., (1989), Nature 341, 197–205
Bissonnette, R. P. et al., (1992), Nature 359, 552–554
Breeden, L. & Nasmyth, K. (1985), Cold Spring Harbor Symp. Quant. Biol. 50, 643–650
Chien, C. T. et al., (1991), Proc. Natl. Acad. Sci. 88, 9578–9582
Clarke, A. R. et al., (1993), Nature 362, 849–852
Cleary, M. L. & Sklar, J., (1985), Proc. Natl. Acad. Sci. USA 82, 7439–7443
Cleary, M. L., (1986), Cell 47, 19–28
Debbas, M. & White, E. (1993), Genes Dev. 7, 546–554
Durfee, T. et al., (1993), Genes Dev. 7, 555–569
Edgington, S. M., (1993) Bio/Technol. 11, 787–792
Fanidi, A. et al., Nature 359, 554–556
Fernandez-Sarabia & Bischoff, (1993), Nature, 366, 274–275
Field, J. et al., (1988), Mol. Cell. Biol. 8, 2159–2165
Fields, S. & Song, O. K., (1989), Nature 340, 245–246
Frohman, M. A. et al., (1988), Proc. Natl. Acad. Sci. USA 85, 8998–9002
Fuerst, T. R. et al., (1986), Proc. Natl. Acad. Sci. USA 83, 8122–8126
Garret, M. D. et al., Biochem. J. 276, 833-836
Gill, G. & Ptashne, M., (1987), Cell 51, 121–126
Gluzman, Y. (1981), Cell 23, 175–181
Gooding, L. R. et al., (1991), J. Virol. 65, 3083–3094
Graham, F. L. et al., (1977), J. Gen. Virol. 36, 59–74
Green, M. et al., (1983), J. Virol. 48, 604–615
Hashimoto, S. et al., (1991), Int. Immunol. 3, 343–351
Henderson, S. et al., (1993), Proc. Natl. Acad. Sci. USA 90, 8479–8488
Hengartner, M. O. et al. (1992), Nature 356, 495–499
Hockenbery, D. et al., (1990), Nature 348, 334–336
Hoffman, C. S. & Winston, F., (1987), Gene 57, 267–272
Hunziker, W. & Schrickel, S, (1988), Mol. Endo. 2, 465–473
Iacopino, A. M. & Christakos, S., (1990), Proc. Natl. Acad. Sci. USA 87, 4078–4082
Itoh, N. et al., (1991), Cell 66, 233–243
Jacobson, M. D. et al., (1993), Nature 361, 365–369
Kishore, G. M. & Shaw, D. M. (1988), Annu. Rev. Biochem. 57, 627–663
Lancaster, C. A. et al., (1994), J. Biol. Chem. 269, 1137–1142
Lane, D. P., (1993), Nature 362, 786–787
Laster, S. M. et al., (1988), J. Immunol. 141, 2629–2643
Liu, Y. J. et al., (1989), Nature, 342, 929–931
Lowe, S. W. et al., (1993), Nature 362, 847–849
Lazebnik, Y. A., et al., (1993), J. Cell Biol. 123, 7–22
Ma, J. & Ptashne, M., (1987), Cell 51, 113–119
Miller, J. H. (1972), "Experiments in Molecular Genetics", Cold Spring Harbor Laboratory, N.Y.
Miura, M. et al., (1993), Cell 75, 653–660
Moss, B. et al., (1990), Nature 348, 91–92
Mymryk, J. S. et al., (1994), Oncogene 9, 1187–1193
Nunez, G. et al., (1990), J. Immunol. 144, 3602–3610
Oltvai, Z. N. et al., (1993), Cell 74, 609–619
Pearson, G. R. et al., (1987), Virology 160, 151–161
Pearson, W. R. & Lipman, D. J., (1988), Proc. Nat. Acad. Sci., USA 85, 2444–2448
Polli, J. W. & Kincaid, R. L., (1992), Proc. Natl. Acad. Sci. USA 89, 11079–11083
Rao, L. et al., (1992), Proc. Natl. Acad. Sci. USA 89, 7742–7746
Repaske, D. R., (1992), J. Biol. Chem. 267, 18683–18688
Rose et al., (1990), "Methods in Yeast Genetics", Cold Spring Harbor Laboratory, N.Y.
Rogers, S. et al., (1986), Science 234, 364–368
Scaria, A. et al., (1992), Virology 191, 743–753
Seto, M. et al., (1988), EMBO J. 7, 123–131
Sentman, C. L. et al., (1991), Cell 67, 879–888
Shiestl, R. H. & Gietz, R. D., (1989), Curr. Genet. 16, 339–346
Sorenson, C. M. & Eastman, A., (1988), Cancer Res. 48, 4484–4488
Stamenkovic, I. & Seed, B., (1990), Nature 345, 74–77
Strasser, A. et al., (1991), Cell 67, 889–899
Studier, F. W. et al., (1990), Methods Enzymol. 185, 60–89
Subramanian T., (1985), Mol. Cell Biol. 5, 3297–3300
Subramanian T., (1993), Gene 124, 173–181
Summerhayes, I. C. et al., (1982), Proc. Natl. Acad. Sci. USA 79, 5292–5296
Tarodi, B. et al., (1993), Intl. J. Oncol. 3, 467–472
Tian, Q. et al., (1991), Cell 67, 629–639
Tsujimoto, Y. & Croce, C., (1986), Proc. Natl. Acad. Sci. USA 83, 5214–5218
Vaux, D., (1993), Proc. Natl. Acad. Sci. USA 90, 786–789
Vaux, D. L. et al., (1991), Science 258, 1955–1957
Vaux, D. L. et al., (1988), Nature 335, 440–442
Watanabe-Fukunaga, R. et al., (1992), Nature 356, 314–317
White, E. et al., (1991), J. Virol. 65, 2968–2978
White, E. et al., (1984b), Mol. Cell Biol. 4, 2865–2875
White, E. et al., (1992), Mol. Cell Biol. 12, 2570–2580
Williams, G. T., (1991), Cell 65, 1097–1098
Williams, G. T. & Smith, C. A., (1993), Cell 74, 777–779
Wilson, G. L. et al., (1991), J. Exptl. Med. 173, 137–146
Wyllie, A. H., (1980), Nature 284, 555–556
Yuan, J. & Horvitz, H. R. (1990), Devel. Biol. 138, 33–41
Yuan, J. & Horvitz, H. R. (1992), Development 116, 309–320
Yuan, J. et al., (1993), Cell 75, 641–652

All references cited herein are incorporated herein by reference in entirety.

As will be evident to the artisan, various modifications and changes can be made without departing from the spirit and scope of the instant invention.

What is claimed:

1. An isolated polypeptide comprising one member selected from the group consisting of SEQ ID NO:21, SEQ ID NO:23, SEQ ID:25, SEQ ID NO:27, and SEQ ID NO:29.

2. An isolated nucleic acid molecule comprising one member selected from the group consisting of SEQ ID NO:20, SEQ ID NO:22, SEQ ID NO:24, SEQ ID NO:26, and SEQ ID NO:28.

3. An isolated polypeptide consisting of one member selected from the group consisting of SEQ ID NO:1, SEQ ID NO:2, SEQ ID:3, SEQ ID NO:4, SEQ ID NO:5, SEQ ID NO:6, SEQ ID NO:7, and SEQ ID NO:32.

4. The polypeptide of claim 3 which is SEQ ID NO:1, SEQ ID NO:2, SEQ ID NO:3 or SEQ ID NO:4.

5. An isolated nucleic acid molecule consisting of a nucleotide sequence that encodes one member selected from the group consisting of SEQ ID NO:1, SEQ ID NO:2, SEQ ID NO:3, SEQ ID NO:4, SEQ ID NO:5, SEQ ID NO:6, SEQ ID NO:7, and SEQ ID NO:32.

6. The nucleic acid molecule of claim 5 that encodes SEQ ID NO:1, SEQ ID NO:2, SEQ ID NO:3 or SEQ ID NO:4.

7. A method for regulating cell death comprising exposing an isolated cell to a cell death regulating amount of a polypeptide comprising one member selected from the group consisting of SEQ ID NO:21, SEQ ID NO:23, SEQ ID NO:25, SEQ ID NO:27, SEQ ID NO:29, and SEQ ID NO:31.

8. The method of claim 7 which comprises transfecting said cell with a nucleic acid molecule that directs the expression of said polypeptide.

9. The method of claim 9, wherein said polypeptide comprises SEQ ID NO:27.

10. The method of claim 8, wherein said nucleic acid molecule comprises one member selected from the group consisting of SEQ ID NO:20, SEQ ID NO:22, SEQ ID NO:24, SEQ ID NO:26, SEQ ID NO:28, and SEQ ID NO:30.

11. The method of claim 9, which comprises transfecting said cell with a nucleic acid molecule comprising SEQ ID NO:26.

12. A method for neutralizing activity of a molecule selected from the group consisting of the E1B 19 kD protein, the Bcl-2 protein, and the BHRF-1 protein, said method comprising exposing an isolated cell to an activity neutralizing amount of a polypeptide comprising one member selected from the group consisting of SEQ ID NO:21, SEQ ID NO:23, SEQ ID NO:25, SEQ ID NO:27, SEQ ID NO:29, and SEQ ID NO:31.

13. The method of claim 12, which comprises transfecting said cell with a nucleic acid molecule that directs the expression of said polypeptide.

14. The method of claim 12 wherein said molecule is Bcl-2.

15. The method of claim 12, wherein said nucleic acid molecule comprises one member selected from the group consisting of SEQ ID NO:20, SEQ ID NO:22, SEQ ID NO:24, SEQ ID NO:26, SEQ ID NO:28, and SEQ ID NO:30.

16. A method for detecting molecules that bind to at least one of the polypeptides recited in step (b), said method comprising:

(a) lysing cells suspected of comprising said molecules to produce a lysate;

(b) exposing said lysate to a polypeptide comprising at least one member selected from the group consisting of SEQ ID NO:21, SEQ ID NO:23, SEQ ID NO:25, SEQ ID NO:27, SEQ ID NO:29, and SEQ ID NO:31; and (c) determining the presence of molecule-polypeptide aggregates, thereby detecting a molecule that binds to at least one of the polypeptides recited in step (b).

17. An isolated nucleic acid molecule consisting of SEQ ID NO:30.

* * * * *

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 9 amino acids
        ( B ) TYPE: amino acid (C) STRANDEDNESS:
(D) TOPOLOGY: linear (ii) MOLECULE TYPE: protein (xi) SEQUENCE DESCRIPTION: SEQ ID NO:1:

Ala Ala Pro Ala Pro Gly Phe Phe Ser
1               5

(2) INFORMATION FOR SEQ ID NO:2:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:2:

Tyr Arg Arg Asp Phe Ala Glu
1               5

(2) INFORMATION FOR SEQ ID NO:3:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:3:

Tyr Lys Trp Glu Phe Glu Glu
1               5

(2) INFORMATION FOR SEQ ID NO:4:

(i) SEQUENCE CHARACTERISTICS:
(A) LENGTH: 9 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:4:

Ala Ala Ala Ala Val Ala Phe Leu Ser
1               5

(2) INFORMATION FOR SEQ ID NO:5:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: protein (ix) FEATURE:
(A) NAME/KEY: Modified-site
(B) LOCATION: 2

(ix) FEATURE:
(A) NAME/KEY: Modified-site
(B) LOCATION: 3

(ix) FEATURE:
(A) NAME/KEY: Modified-site
(B) LOCATION: 4

( i x ) FEATURE:
    ( A ) NAME/KEY: Modified-site
    ( B ) LOCATION: 6

( x i ) SEQUENCE DESCRIPTION: SEQ ID NO:5:

```
Tyr  Xaa  Xaa  Xaa  Phe  Xaa  Glu
 1                     5
```

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Modified-site
        ( B ) LOCATION: 3

( i x ) FEATURE:
        ( A ) NAME/KEY: Modified-site
        ( B ) LOCATION: 5

( i x ) FEATURE:
        ( A ) NAME/KEY: Modified-site
        ( B ) LOCATION: 7

( x i ) SEQUENCE DESCRIPTION: SEQ ID NO:6:

```
Ala  Ala  Xaa  Ala  Xaa  Phe  Xaa  Ser
 1                     5
```

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:7:

```
Ala  Ala  Pro  Ala  Pro  Gly  Ile  Phe  Ser
 1                     5
```

( 2 ) INFORMATION FOR SEQ ID NO:8:

( i ) SEQUENCE CHARACTERISTICS:
        ( A ) LENGTH: 175 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:8:

```
Met  Glu  Ala  Trp  Glu  Cys  Leu  Glu  Asp  Phe  Ser  Ala  Val  Arg  Asn  Leu
 1                     5                    10                            15

Leu  Glu  Gln  Ser  Ser  Asn  Ser  Thr  Ser  Trp  Phe  Trp  Arg  Phe  Leu  Trp
                      20                    25                            30

Gly  Ser  Ser  Gln  Ala  Lys  Leu  Val  Cys  Arg  Ile  Lys  Glu  Asp  Tyr  Lys
                      35                    40                            45

Trp  Glu  Phe  Glu  Glu  Leu  Leu  Lys  Ser  Cys  Gly  Glu  Leu  Phe  Asp  Ser
                50                          55                    60

Leu  Asn  Leu  Gly  His  Gln  Ala  Leu  Phe  Gln  Glu  Lys  Val  Ile  Lys  Thr
```

```
                65                       70                      75                       80
      Leu  Asp  Phe  Ser  Thr  Pro  Gly  Arg  Ala  Ala  Ala  Val  Ala  Phe  Leu
                          85                      90                       95

Ser  Phe  Ile  Lys  Asp  Lys  Trp  Ser  Glu  Glu  Thr  His  Leu  Ser  Gly  Gly
                     100                      105                     110

Tyr  Leu  Leu  Asp  Phe  Leu  Ala  Met  His  Leu  Trp  Arg  Ala  Val  Val  Arg
                     115                      120                     125

His  Lys  Asn  Arg  Leu  Leu  Leu  Leu  Ser  Ser  Val  Arg  Pro  Ala  Ile  Ile
                130                      135                      140

Pro  Thr  Glu  Glu  Gln  Gln  Gln  Glu  Glu  Ala  Arg  Arg  Arg  Arg  Arg  Gln
      145                           150                      155                      160

Glu  Gln  Ser  Pro  Trp  Asn  Pro  Arg  Ala  Gly  Leu  Asp  Pro  Arg  Glu
                          165                      170                     175
```

( 2 ) INFORMATION FOR SEQ ID NO:9:

( i ) SEQUENCE CHARACTERISTICS:
        ( A ) LENGTH: 175 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:9:

```
      Met  Glu  Ala  Trp  Glu  Cys  Leu  Glu  Asp  Phe  Ser  Ala  Val  Ala  Ser  Leu
      1                   5                       10                          15

Leu  Glu  Gln  Ser  Ser  Asn  Ser  Thr  Ser  Trp  Phe  Trp  Arg  Phe  Leu  Trp
                     20                       25                      30

Gly  Ser  Ser  Gln  Ala  Lys  Leu  Val  Cys  Arg  Ile  Lys  Glu  Asp  Tyr  Lys
                     35                       40                      45

Trp  Glu  Phe  Glu  Glu  Leu  Leu  Lys  Ser  Cys  Gly  Glu  Leu  Phe  Asp  Ser
                50                       55                      60

Leu  Asn  Leu  Gly  His  Gln  Ala  Leu  Phe  Gln  Glu  Lys  Val  Ile  Lys  Thr
      65                       70                      75                       80

Leu  Asp  Phe  Ser  Thr  Pro  Gly  Arg  Ala  Ala  Ala  Val  Ala  Phe  Leu
                          85                      90                       95

Ser  Phe  Ile  Lys  Asp  Lys  Trp  Ser  Glu  Glu  Thr  His  Leu  Ser  Gly  Gly
                     100                      105                     110

Tyr  Leu  Leu  Asp  Phe  Leu  Ala  Met  His  Leu  Trp  Arg  Ala  Val  Val  Arg
                     115                      120                     125

His  Lys  Asn  Arg  Leu  Leu  Leu  Leu  Ser  Ser  Val  Arg  Pro  Ala  Ile  Ile
                130                      135                      140

Pro  Thr  Glu  Glu  Gln  Gln  Gln  Glu  Glu  Ala  Arg  Arg  Arg  Arg  Arg  Gln
      145                           150                      155                      160

Glu  Gln  Ser  Pro  Trp  Asn  Pro  Arg  Ala  Gly  Leu  Asp  Pro  Arg  Glu
                          165                      170                     175
```

( 2 ) INFORMATION FOR SEQ ID NO:10:

( i ) SEQUENCE CHARACTERISTICS:
        ( A ) LENGTH: 175 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:10:

```
      Met  Glu  Ala  Trp  Glu  Cys  Leu  Glu  Asp  Phe  Ser  Ala  Val  Arg  Asn  Leu
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |

Leu Glu Gln Ser Ser Asn Ser Thr Ser Trp Phe Trp Ala Ser Leu Trp
                    20                  25                  30

Gly Ser Ser Gln Ala Lys Leu Val Cys Arg Ile Lys Glu Asp Tyr Lys
            35                  40                  45

Trp Glu Phe Glu Glu Leu Leu Lys Ser Cys Gly Glu Leu Phe Asp Ser
        50                  55                  60

Leu Asn Leu Gly His Gln Ala Leu Phe Gln Glu Lys Val Ile Lys Thr
65                      70                  75                      80

Leu Asp Phe Ser Thr Pro Gly Arg Ala Ala Ala Ala Val Ala Phe Leu
                85                  90                  95

Ser Phe Ile Lys Asp Lys Trp Ser Glu Glu Thr His Leu Ser Gly Gly
            100                 105                 110

Tyr Leu Leu Asp Phe Leu Ala Met His Leu Trp Arg Ala Val Val Arg
        115                 120                 125

His Lys Asn Arg Leu Leu Leu Leu Ser Ser Val Arg Pro Ala Ile Ile
    130                 135                 140

Pro Thr Glu Glu Gln Gln Gln Glu Glu Ala Arg Arg Arg Arg Arg Gln
145                 150                 155                 160

Glu Gln Ser Pro Trp Asn Pro Arg Ala Gly Leu Asp Pro Arg Glu
                165                 170                 175

( 2 ) INFORMATION FOR SEQ ID NO:11:

( i ) SEQUENCE CHARACTERISTICS:
        ( A ) LENGTH: 175 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:11:

Met Glu Ala Trp Glu Cys Leu Glu Asp Phe Ser Ala Val Arg Asn Leu
1               5                   10                  15

Leu Glu Gln Ser Ser Asn Ser Thr Ser Trp Phe Trp Arg Phe Leu Trp
                    20                  25                  30

Gly Ser Ser Gln Ala Lys Leu Val Cys Arg Ile Lys Glu Asp Tyr Lys
            35                  40                  45

Trp Ala Ser Glu Glu Leu Leu Lys Ser Cys Gly Glu Leu Phe Asp Ser
        50                  55                  60

Leu Asn Leu Gly His Gln Ala Leu Phe Gln Glu Lys Val Ile Lys Thr
65                      70                  75                      80

Leu Asp Phe Ser Thr Pro Gly Arg Ala Ala Ala Ala Val Ala Phe Leu
                85                  90                  95

Ser Phe Ile Lys Asp Lys Trp Ser Glu Glu Thr His Leu Ser Gly Gly
            100                 105                 110

Tyr Leu Leu Asp Phe Leu Ala Met His Leu Trp Arg Ala Val Val Arg
        115                 120                 125

His Lys Asn Arg Leu Leu Leu Leu Ser Ser Val Arg Pro Ala Ile Ile
    130                 135                 140

Pro Thr Glu Glu Gln Gln Gln Glu Glu Ala Arg Arg Arg Arg Arg Gln
145                 150                 155                 160

Glu Gln Ser Pro Trp Asn Pro Arg Ala Gly Leu Asp Pro Arg Glu
                165                 170                 175

( 2 ) INFORMATION FOR SEQ ID NO:12:

( i ) SEQUENCE CHARACTERISTICS:
  ( A ) LENGTH: 175 amino acids
  ( B ) TYPE: amino acid
  ( C ) STRANDEDNESS:
  ( D ) TOPOLOGY: linear ( i i ) MOLECULE TYPE: protein ( x i ) SEQUENCE DESCRIPTION: SEQ ID NO:12:

```
Met Glu Ala Trp Glu Cys Leu Glu Asp Phe Ser Ala Val Arg Asn Leu
 1               5                  10                  15

Leu Glu Gln Ser Ser Asn Ser Thr Ser Trp Phe Trp Arg Phe Leu Trp
                20                  25                  30

Gly Ser Ser Gln Ala Lys Leu Val Cys Arg Ile Lys Glu Asp Tyr Lys
            35                  40                  45

Trp Glu Phe Glu Glu Leu Leu Lys Ser Cys Gly Glu Leu Phe Asp Ser
        50                  55                  60

Leu Asn Leu Gly His Gln Ala Leu Phe Gln Ala Ser Val Ile Lys Thr
65                  70                  75                  80

Leu Asp Phe Ser Thr Pro Gly Arg Ala Ala Ala Ala Val Ala Phe Leu
                85                  90                  95

Ser Phe Ile Lys Asp Lys Trp Ser Glu Glu Thr His Leu Ser Gly Gly
               100                 105                 110

Tyr Leu Leu Asp Phe Leu Ala Met His Leu Trp Arg Ala Val Val Arg
           115                 120                 125

His Lys Asn Arg Leu Leu Leu Leu Ser Ser Val Arg Pro Ala Ile Ile
           130                 135                 140

Pro Thr Glu Glu Gln Gln Gln Glu Glu Ala Arg Arg Arg Arg Arg Gln
145                 150                 155                 160

Glu Gln Ser Pro Trp Asn Pro Arg Ala Gly Leu Asp Pro Arg Glu
               165                 170                 175
```

( 2 ) INFORMATION FOR SEQ ID NO:13:

( i ) SEQUENCE CHARACTERISTICS:
    ( A ) LENGTH: 168 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:13:

```
Met Glu Ala Trp Glu Cys Leu Glu Asp Phe Ser Ala Val Arg Asn Leu
 1               5                  10                  15

Leu Glu Gln Ser Ser Asn Ser Thr Ser Trp Phe Trp Arg Phe Leu Trp
                20                  25                  30

Gly Ser Ser Gln Ala Lys Leu Val Cys Arg Ile Lys Glu Asp Tyr Lys
            35                  40                  45

Trp Glu Phe Glu Glu Leu Leu Lys Ser Cys Gly Glu Leu Phe Asp Ser
        50                  55                  60

Leu Asn Leu Gly His Gln Ala Leu Phe Gln Glu Lys Val Ile Lys Thr
65                  70                  75                  80

Leu Asp Phe Ser Thr Pro Gly Arg Ala Ser Phe Ile Lys Asp Lys Trp
                85                  90                  95

Ser Glu Glu Thr His Leu Ser Gly Gly Tyr Leu Leu Asp Phe Leu Ala
               100                 105                 110

Met His Leu Trp Arg Ala Val Val Arg His Lys Asn Arg Leu Leu Leu
           115                 120                 125
```

| | | | | | | | | | | | | | | |
|---|---|---|---|---|---|---|---|---|---|---|---|---|---|---|
|Leu|Ser|Ser|Val|Arg|Pro|Ala|Ile|Ile|Pro|Thr|Glu|Gln|Gln|Gln|
| |130| | | |135| | | | |140| | | | |
|Glu|Glu|Ala|Arg|Arg|Arg|Arg|Gln|Glu|Gln|Ser|Pro|Trp|Asn|Pro|
|145| | | | |150| | | |155| | | | |160|
|Arg|Ala|Gly|Leu|Asp|Pro|Arg|Glu| | | | | | | |
| | | | |165| | | | | | | | | | |

(2) INFORMATION FOR SEQ ID NO:14:

(i) SEQUENCE CHARACTERISTICS:
        (A) LENGTH: 175 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

| | | | | | | | | | | | | | | |
|---|---|---|---|---|---|---|---|---|---|---|---|---|---|---|
|Met|Glu|Ala|Trp|Glu|Cys|Leu|Glu|Asp|Phe|Ser|Ala|Val|Arg|Asn|Leu|
|1| | | |5| | | | |10| | | | |15|
|Leu|Glu|Gln|Ser|Ser|Asn|Ser|Thr|Ser|Trp|Phe|Trp|Arg|Phe|Leu|Trp|
| | | | |20| | | |25| | | | |30| |
|Gly|Ser|Ser|Gln|Ala|Lys|Leu|Val|Cys|Arg|Ile|Lys|Glu|Asp|Tyr|Lys|
| | |35| | | | |40| | | | |45| | |
|Trp|Glu|Phe|Glu|Glu|Leu|Leu|Lys|Ser|Cys|Gly|Glu|Leu|Phe|Asp|Ser|
| |50| | | | |55| | | | |60| | | |
|Leu|Asn|Leu|Gly|His|Gln|Ala|Leu|Phe|Gln|Glu|Lys|Val|Ile|Lys|Thr|
|65| | | | |70| | | | |75| | | | |80|
|Leu|Asp|Phe|Ser|Thr|Pro|Gly|Arg|Ala|Ala|Ala|Ala|Val|Ala|Phe|Leu|
| | | | |85| | | | |90| | | | |95| |
|Ser|Phe|Ile|Lys|Asp|Lys|Trp|Ser|Glu|Glu|Thr|His|Leu|Ser|Gly|Gly|
| | | |100| | | | |105| | | | |110| | |
|Tyr|Leu|Leu|Asp|Phe|Leu|Ala|Met|His|Leu|Ala|Ser|Ala|Val|Val|Arg|
| | |115| | | | |120| | | | |125| | | |
|His|Lys|Asn|Arg|Leu|Leu|Leu|Leu|Ser|Ser|Val|Arg|Pro|Ala|Ile|Ile|
| |130| | | | |135| | | | |140| | | | |
|Pro|Thr|Glu|Glu|Gln|Gln|Gln|Glu|Glu|Ala|Arg|Arg|Arg|Arg|Arg|Gln|
|145| | | | |150| | | | |155| | | | |160|
|Glu|Gln|Ser|Pro|Trp|Asn|Pro|Arg|Ala|Gly|Leu|Asp|Pro|Arg|Glu| |
| | | | |165| | | | |170| | | | |175| |

(2) INFORMATION FOR SEQ ID NO:15:

(i) SEQUENCE CHARACTERISTICS:
        (A) LENGTH: 147 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:15:

| | | | | | | | | | | | | | | |
|---|---|---|---|---|---|---|---|---|---|---|---|---|---|---|
|Met|Glu|Ala|Trp|Glu|Cys|Leu|Glu|Asp|Phe|Ser|Ala|Val|Arg|Asn|Leu|
|1| | | |5| | | | |10| | | | |15|
|Leu|Glu|Gln|Ser|Ser|Asn|Ser|Thr|Ser|Trp|Phe|Trp|Arg|Phe|Leu|Trp|
| | | | |20| | | |25| | | | |30| |
|Gly|Ser|Ser|Gln|Ala|Lys|Leu|Val|Cys|Arg|Ile|Lys|Glu|Asp|Tyr|Lys|
| | |35| | | | |40| | | | |45| | |
|Trp|Glu|Phe|Glu|Glu|Leu|Leu|Lys|Ser|Cys|Gly|Glu|Leu|Phe|Asp|Ser|
| |50| | | | |55| | | | |60| | | |

|  |  |  |  |  |  |  |  |  |  |  |  |  |  |  |
|---|---|---|---|---|---|---|---|---|---|---|---|---|---|---|
| Leu | Asn | Leu | Gly | His | Gln | Ala | Leu | Phe | Gln | Glu | Lys | Val | Ile | Lys | Thr |
| 65 |  |  |  | 70 |  |  |  | 75 |  |  |  |  |  | 80 |

Leu Asp Phe Ser Thr Pro Gly Arg Ala Ala Ala Val Ala Phe Leu
65             85                 90                95

Leu Asp Phe Ser Thr Pro Gly Arg Ala Ala Ala Val Ala Phe Leu
                    85                      90                      95

Ser Phe Ile Lys Asp Lys Trp Ser Glu Thr His Leu Ser Gly Gly
            100                 105                 110

Tyr Leu Leu Asp Phe Leu Ala Met His Leu Trp Arg Ala Val Val Arg
        115                 120                 125

His Lys Asn Arg Leu Leu Leu Ser Ser Val Arg Pro Ala Ile Ile
    130                 135                 140

Pro Thr Ser
145

(2) INFORMATION FOR SEQ ID NO:16:

(i) SEQUENCE CHARACTERISTICS:
        (A) LENGTH: 239 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

Met Ala His Ala Gly Arg Ser Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Phe
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Cys Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
            165                 170                 175

Met Thr Glu Tyr Leu Asn Arg His Leu His Thr Trp Ile Gln Asp Asn
        180                 185                 190

Gly Gly Trp Asp Ala Phe Val Glu Leu Tyr Gly Pro Ser Met Arg Pro
    195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

(2) INFORMATION FOR SEQ ID NO:17:

(i) SEQUENCE CHARACTERISTICS:
  (A) LENGTH: 232 amino acids
  (B) TYPE: amino acid
  (C) STRANDEDNESS:
  (D) TOPOLOGY: linear (ii) MOLECULE TYPE: protein (xi) SEQUENCE DESCRIPTION: SEQ ID NO:17:

| Met | Ala | His | Ala | Gly | Arg | Ser | Gly | Tyr | Asp | Asn | Arg | Glu | Ile | Val | Met |
|---|---|---|---|---|---|---|---|---|---|---|---|---|---|---|---|
| 1 | | | | 5 | | | | | 10 | | | | | | 15 |

| Lys | Tyr | Ile | His | Tyr | Lys | Leu | Ser | Gln | Arg | Gly | Tyr | Glu | Trp | Asp | Ala |
|---|---|---|---|---|---|---|---|---|---|---|---|---|---|---|---|
| | | | 20 | | | | | 25 | | | | | 30 | | |

| Gly | Asp | Val | Gly | Ala | Ala | Pro | Pro | Gly | Phe | Ser | Ser | Gln | Pro | Gly | His |
|---|---|---|---|---|---|---|---|---|---|---|---|---|---|---|---|
| | | 35 | | | | | 40 | | | | | 45 | | | |

| Thr | Pro | His | Pro | Ala | Ala | Ser | Arg | Asp | Pro | Val | Ala | Arg | Thr | Ser | Pro |
|---|---|---|---|---|---|---|---|---|---|---|---|---|---|---|---|
| | 50 | | | | | 55 | | | | | 60 | | | | |

| Leu | Gln | Thr | Pro | Ala | Ala | Pro | Gly | Ala | Ala | Ala | Gly | Pro | Ala | Leu | Ser |
|---|---|---|---|---|---|---|---|---|---|---|---|---|---|---|---|
| 65 | | | | | 70 | | | | | 75 | | | | | 80 |

| Pro | Val | Pro | Pro | Val | Val | His | Leu | Thr | Leu | Arg | Gln | Ala | Gly | Asp | Asp |
|---|---|---|---|---|---|---|---|---|---|---|---|---|---|---|---|
| | | | | 85 | | | | | 90 | | | | | 95 | |

| Phe | Ser | Arg | Arg | Tyr | Arg | Arg | Asp | Phe | Ala | Glu | Met | Ser | Ser | Gln | Leu |
|---|---|---|---|---|---|---|---|---|---|---|---|---|---|---|---|
| | | | 100 | | | | | 105 | | | | | 110 | | |

| His | Leu | Thr | Pro | Phe | Thr | Ala | Arg | Gly | Cys | Phe | Ala | Thr | Val | Val | Glu |
|---|---|---|---|---|---|---|---|---|---|---|---|---|---|---|---|
| | | 115 | | | | | 120 | | | | | 125 | | | |

| Glu | Leu | Phe | Arg | Asp | Gly | Val | Asn | Trp | Gly | Arg | Ile | Val | Ala | Phe | Phe |
|---|---|---|---|---|---|---|---|---|---|---|---|---|---|---|---|
| | 130 | | | | | 135 | | | | | 140 | | | | |

| Glu | Phe | Gly | Gly | Val | Met | Cys | Val | Glu | Ser | Val | Asn | Arg | Glu | Met | Ser |
|---|---|---|---|---|---|---|---|---|---|---|---|---|---|---|---|
| 145 | | | | | 150 | | | | | 155 | | | | | 160 |

| Pro | Leu | Val | Asp | Asn | Ile | Ala | Leu | Trp | Met | Thr | Glu | Tyr | Leu | Asn | Arg |
|---|---|---|---|---|---|---|---|---|---|---|---|---|---|---|---|
| | | | | 165 | | | | | 170 | | | | | 175 | |

| His | Leu | His | Thr | Trp | Ile | Gln | Asp | Asn | Gly | Gly | Trp | Asp | Ala | Phe | Val |
|---|---|---|---|---|---|---|---|---|---|---|---|---|---|---|---|
| | | | 180 | | | | | 185 | | | | | 190 | | |

| Glu | Leu | Tyr | Gly | Pro | Ser | Met | Arg | Pro | Leu | Phe | Asp | Phe | Ser | Trp | Leu |
|---|---|---|---|---|---|---|---|---|---|---|---|---|---|---|---|
| | | 195 | | | | | 200 | | | | | 205 | | | |

| Ser | Leu | Lys | Thr | Leu | Leu | Ser | Leu | Ala | Leu | Val | Gly | Ala | Cys | Ile | Thr |
|---|---|---|---|---|---|---|---|---|---|---|---|---|---|---|---|
| | 210 | | | | | 215 | | | | | 220 | | | | |

| Leu | Gly | Ala | Tyr | Leu | Gly | His | Lys |
|---|---|---|---|---|---|---|---|
| 225 | | | | | 230 | | |

(2) INFORMATION FOR SEQ ID NO:18:

(i) SEQUENCE CHARACTERISTICS:
  (A) LENGTH: 232 amino acids
  (B) TYPE: amino acid
  (C) STRANDEDNESS:
  (D) TOPOLOGY: linear (ii) MOLECULE TYPE: protein (xi) SEQUENCE DESCRIPTION: SEQ ID NO:18:

| Met | Ala | His | Ala | Gly | Arg | Ser | Gly | Tyr | Asp | Asn | Arg | Glu | Ile | Val | Met |
|---|---|---|---|---|---|---|---|---|---|---|---|---|---|---|---|
| 1 | | | | 5 | | | | | 10 | | | | | | 15 |

| Lys | Tyr | Ile | His | Tyr | Lys | Leu | Ser | Gln | Arg | Gly | Tyr | Glu | Trp | Asp | Ala |
|---|---|---|---|---|---|---|---|---|---|---|---|---|---|---|---|
| | | | 20 | | | | | 25 | | | | | 30 | | |

| Gly | Asp | Val | Gly | Ala | Ala | Pro | Pro | Gly | Ala | Ala | Pro | Ala | Pro | Gly | Phe |
|---|---|---|---|---|---|---|---|---|---|---|---|---|---|---|---|
| | | 35 | | | | | 40 | | | | | 45 | | | |

| Phe | Ser | Ser | Gln | Pro | Gly | His | Thr | Pro | His | Pro | Ala | Ala | Ser | Arg | Asp |
|---|---|---|---|---|---|---|---|---|---|---|---|---|---|---|---|
| | 50 | | | | | 55 | | | | | 60 | | | | |

|  |  |  |  |  |  |  |  |  |  |  |  |  |  |  |
|---|---|---|---|---|---|---|---|---|---|---|---|---|---|---|
| Pro | Val | Ala | Arg | Thr | Ser | Pro | Leu | Gln | Thr | Pro | Ala | Ala | Pro | Gly | Ser |
| 65 |  |  |  |  | 70 |  |  |  |  | 75 |  |  |  |  | 80 |
| Pro | Val | Pro | Pro | Val | Val | His | Leu | Thr | Leu | Arg | Gln | Ala | Gly | Asp | Asp |
|  |  |  |  | 85 |  |  |  |  | 90 |  |  |  |  | 95 |  |
| Phe | Ser | Arg | Arg | Tyr | Arg | Arg | Asp | Phe | Ala | Glu | Met | Ser | Ser | Gln | Leu |
|  |  |  | 100 |  |  |  |  | 105 |  |  |  |  | 110 |  |  |
| His | Leu | Thr | Pro | Phe | Thr | Ala | Arg | Gly | Cys | Phe | Ala | Thr | Val | Val | Glu |
|  |  | 115 |  |  |  |  | 120 |  |  |  |  | 125 |  |  |  |
| Glu | Leu | Phe | Arg | Asp | Gly | Val | Asn | Trp | Gly | Arg | Ile | Val | Ala | Phe | Phe |
|  | 130 |  |  |  |  | 135 |  |  |  |  | 140 |  |  |  |  |
| Glu | Phe | Gly | Gly | Val | Met | Cys | Val | Glu | Ser | Val | Asn | Arg | Glu | Met | Ser |
| 145 |  |  |  |  | 150 |  |  |  |  | 155 |  |  |  |  | 160 |
| Pro | Leu | Val | Asp | Asn | Ile | Ala | Leu | Trp | Met | Thr | Glu | Tyr | Leu | Asn | Arg |
|  |  |  |  | 165 |  |  |  |  | 170 |  |  |  |  | 175 |  |
| His | Leu | His | Thr | Trp | Ile | Gln | Asp | Asn | Gly | Gly | Trp | Asp | Ala | Phe | Val |
|  |  |  | 180 |  |  |  |  | 185 |  |  |  |  | 190 |  |  |
| Glu | Leu | Tyr | Gly | Pro | Ser | Met | Arg | Pro | Leu | Phe | Asp | Phe | Ser | Trp | Leu |
|  |  | 195 |  |  |  |  | 200 |  |  |  |  | 205 |  |  |  |
| Ser | Leu | Lys | Thr | Leu | Leu | Ser | Leu | Ala | Leu | Val | Gly | Ala | Cys | Ile | Thr |
|  | 210 |  |  |  |  | 215 |  |  |  |  | 220 |  |  |  |  |
| Leu | Gly | Ala | Tyr | Leu | Gly | His | Lys |  |  |  |  |  |  |  |  |
| 225 |  |  |  |  | 230 |  |  |  |  |  |  |  |  |  |  |

(2) INFORMATION FOR SEQ ID NO:19:

(i) SEQUENCE CHARACTERISTICS:
        (A) LENGTH: 229 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:19:

|  |  |  |  |  |  |  |  |  |  |  |  |  |  |  |  |
|---|---|---|---|---|---|---|---|---|---|---|---|---|---|---|---|
| Met | Ala | His | Ala | Gly | Arg | Ser | Gly | Tyr | Asp | Asn | Arg | Glu | Ile | Val | Met |
| 1 |  |  |  | 5 |  |  |  |  | 10 |  |  |  |  | 15 |  |
| Lys | Tyr | Ile | His | Tyr | Lys | Leu | Ser | Gln | Arg | Gly | Tyr | Glu | Trp | Asp | Ala |
|  |  |  | 20 |  |  |  |  | 25 |  |  |  |  | 30 |  |  |
| Gly | Asp | Val | Gly | Ala | Ala | Pro | Pro | Gly | Ala | Ala | Pro | Ala | Pro | Gly | Phe |
|  |  |  | 35 |  |  |  |  | 40 |  |  |  |  | 45 |  |  |
| Phe | Ser | Ser | Gln | Pro | Gly | His | Thr | Pro | His | Pro | Ala | Ala | Ser | Arg | Asp |
|  |  | 50 |  |  |  |  | 55 |  |  |  |  | 60 |  |  |  |
| Pro | Val | Ala | Arg | Thr | Ser | Pro | Leu | Gln | Thr | Pro | Ala | Ala | Pro | Gly | Ala |
| 65 |  |  |  |  | 70 |  |  |  |  | 75 |  |  |  |  | 80 |
| Ala | Ala | Gly | Pro | Ala | Leu | Ser | Pro | Val | Pro | Pro | Val | Val | His | Leu | Thr |
|  |  |  |  | 85 |  |  |  |  | 90 |  |  |  |  | 95 |  |
| Leu | Arg | Gln | Ala | Gly | Asp | Asp | Phe | Ser | Ser | Ser | Gln | Leu | His | Leu | Thr |
|  |  |  | 100 |  |  |  |  | 105 |  |  |  |  | 110 |  |  |
| Pro | Phe | Thr | Ala | Arg | Gly | Cys | Phe | Ala | Thr | Val | Val | Glu | Glu | Leu | Phe |
|  |  | 115 |  |  |  |  | 120 |  |  |  |  | 125 |  |  |  |
| Arg | Asp | Gly | Val | Asn | Trp | Gly | Arg | Ile | Val | Ala | Phe | Phe | Glu | Phe | Gly |
|  | 130 |  |  |  |  | 135 |  |  |  |  | 140 |  |  |  |  |
| Gly | Val | Met | Cys | Val | Glu | Ser | Val | Asn | Arg | Glu | Met | Ser | Pro | Leu | Val |
| 145 |  |  |  |  | 150 |  |  |  |  | 155 |  |  |  |  | 160 |
| Asp | Asn | Ile | Ala | Leu | Trp | Met | Thr | Glu | Tyr | Leu | Asn | Arg | His | Leu | His |
|  |  |  |  | 165 |  |  |  |  | 170 |  |  |  |  | 175 |  |
| Thr | Trp | Ile | Gln | Asp | Asn | Gly | Gly | Trp | Asp | Ala | Phe | Val | Glu | Leu | Tyr |

|  |  |  |  |  |  | 180 |  |  |  | 185 |  |  |  | 190 |  |  |
|---|---|---|---|---|---|---|---|---|---|---|---|---|---|---|---|---|
|  | Gly | Pro | Ser | Met | Arg | Pro | Leu | Phe | Asp | Phe | Ser | Trp | Leu | Ser | Leu | Lys |
|  |  |  | 195 |  |  |  | 200 |  |  |  |  | 205 |  |  |  |  |
|  | Thr | Leu | Leu | Ser | Leu | Ala | Leu | Val | Gly | Ala | Cys | Ile | Thr | Leu | Gly | Ala |
|  |  |  | 210 |  |  | 215 |  |  |  |  | 220 |  |  |  |  |  |
|  | Tyr | Leu | Gly | His | Lys |  |  |  |  |  |  |  |  |  |  |  |
|  |  |  | 225 |  |  |  |  |  |  |  |  |  |  |  |  |  |

( 2 ) INFORMATION FOR SEQ ID NO:20:

( i ) SEQUENCE CHARACTERISTICS:
        ( A ) LENGTH: 1101 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 11..694

( x i ) SEQUENCE DESCRIPTION: SEQ ID NO:20:

```
AGTCCCCAAC ATG GCG GCT CCC CAA GAC GTC CAC GTC CGG ATC TGT AAC        49
           Met Ala Ala Pro Gln Asp Val His Val Arg Ile Cys Asn
             1               5                  10

CAA GAG ATT GTC AAA TTT GAC CTG GAG GTG AAG GCG CTT ATT CAG GAT        97
Gln Glu Ile Val Lys Phe Asp Leu Glu Val Lys Ala Leu Ile Gln Asp
         15              20                  25

ATC CGT GAT TGT TCA GGA CCC TTA AGT GCT CTT ACT GAA CTG AAT ACT       145
Ile Arg Asp Cys Ser Gly Pro Leu Ser Ala Leu Thr Glu Leu Asn Thr
 30              35                  40                      45

AAA GTA AAA GAG AAA TTT CAA CAG TTG CGT CAC AGA ATA CAG GAC CTG       193
Lys Val Lys Glu Lys Phe Gln Gln Leu Arg His Arg Ile Gln Asp Leu
                 50                  55                  60

GAG CAG TTG GCT AAA GAG CAA GAC AAA GAA TCA GAG AAA CAA CTT CTA       241
Glu Gln Leu Ala Lys Glu Gln Asp Lys Glu Ser Glu Lys Gln Leu Leu
             65                  70                  75

CTC CAG GAA GTG GAG AAT CAC AAA AAG CAG ATG CTC AGC AAT CAG GCC       289
Leu Gln Glu Val Glu Asn His Lys Lys Gln Met Leu Ser Asn Gln Ala
         80                  85                  90

TCA TGG AGG AAA GCT AAT CTC ACC TGC AAA ATT GCA ATC GAC AAT CTA       337
Ser Trp Arg Lys Ala Asn Leu Thr Cys Lys Ile Ala Ile Asp Asn Leu
     95                 100                 105

GAG AAA GCA GAA CTT CTT CAG GGA GGA GAT CTC TTA AGG CAA AGG AAA       385
Glu Lys Ala Glu Leu Leu Gln Gly Gly Asp Leu Leu Arg Gln Arg Lys
110             115                 120                 125

ACC ACC AAA GAG AGC CTG GCC CAG ACA TCC AGT ACC ATC ACT GAG AGC       433
Thr Thr Lys Glu Ser Leu Ala Gln Thr Ser Ser Thr Ile Thr Glu Ser
                130                 135                 140

CTC ATG GGG ATC AGC AGG ATG ATG GCC CAG CAG GTC CAG CAG AGC GAG       481
Leu Met Gly Ile Ser Arg Met Met Ala Gln Gln Val Gln Gln Ser Glu
            145                 150                 155

GAG GCC ATG CAG TCT CTA GTC ACT TCT TCA CGA ACG ATC CTG GAT GCA       529
Glu Ala Met Gln Ser Leu Val Thr Ser Ser Arg Thr Ile Leu Asp Ala
        160                 165                 170

AAT GAA GAA TTT AAG TCC ATG TCG GGC ACC ATC CAG CTG GGC CGG AAG       577
Asn Glu Glu Phe Lys Ser Met Ser Gly Thr Ile Gln Leu Gly Arg Lys
    175                 180                 185

CTT ATC ACA AAA TAC AAT CGC CGG GAG CTG ACG GAC AAG CTT CTC ATC       625
Leu Ile Thr Lys Tyr Asn Arg Arg Glu Leu Thr Asp Lys Leu Leu Ile
190                 195                 200                 205
```

```
TTC  CTT  GCG  CTA  CGC  CTG  TTT  CTT  GCT  ACG  GTC  CTC  TAT  ATT  GTG  AAA         673
Phe  Leu  Ala  Leu  Arg  Leu  Phe  Leu  Ala  Thr  Val  Leu  Tyr  Ile  Val  Lys
               210                      215                          220

AAG  CGG  CTC  TTT  CCA  TTT  TTG  TGAGATCCCA  AAGGTGCCAG  TTCTGGCCCT                 724
Lys  Arg  Leu  Phe  Pro  Phe  Leu
               225

TTCAGCTCCT  GTTTCAGGAT  CTGTCCTGGT  TCCTGAGCTC  TAGGCTGCTA  AGCTGAGCCA                784

CACACCCCTC  CGTTTTGCAC  CAGTTGCCTG  CAGGTTGGAT  GGAACACAGT  GCCCCACTTT                844

TCTGCAAGTA  GCTGGCTTGT  AAAGGGTGAA  CAGAGCCATG  GGAGGAAGGT  CTGGCATTGG                904

GATGCCGCCC  TGGGGACATA  CGAACCGCCT  CCTTCCACCA  TTGTGCACTA  TGGGAGGCCG                964

CTGCTGCGTG  GAGCACTTAA  AGTCCAGCCT  CCAGGACCGG  ATGCCCTCC   TGTCTCCCGC               1024

TCCCATCGTG  CCCTTAAATG  CCAGATCTGG  TGGAGGGAAG  AGAGAAGAGG  TAGGAAGAAA               1084

GGTGATGAAA  ACTCCTG                                                                  1101
```

( 2 ) INFORMATION FOR SEQ ID NO:21:

( i ) SEQUENCE CHARACTERISTICS:
        ( A ) LENGTH: 228 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Met  Ala  Ala  Pro  Gln  Asp  Val  His  Val  Arg  Ile  Cys  Asn  Gln  Glu  Ile
 1              5                        10                         15

Val  Lys  Phe  Asp  Leu  Glu  Val  Lys  Ala  Leu  Ile  Gln  Asp  Ile  Arg  Asp
               20                        25                         30

Cys  Ser  Gly  Pro  Leu  Ser  Ala  Leu  Thr  Glu  Leu  Asn  Thr  Lys  Val  Lys
               35                        40                         45

Glu  Lys  Phe  Gln  Gln  Leu  Arg  His  Arg  Ile  Gln  Asp  Leu  Glu  Gln  Leu
          50                        55                   60

Ala  Lys  Glu  Gln  Asp  Lys  Glu  Ser  Glu  Lys  Gln  Leu  Leu  Leu  Gln  Glu
 65                       70                        75                        80

Val  Glu  Asn  His  Lys  Lys  Gln  Met  Leu  Ser  Asn  Gln  Ala  Ser  Trp  Arg
                    85                        90                         95

Lys  Ala  Asn  Leu  Thr  Cys  Lys  Ile  Ala  Ile  Asp  Asn  Leu  Glu  Lys  Ala
                    100                       105                        110

Glu  Leu  Leu  Gln  Gly  Gly  Asp  Leu  Leu  Arg  Gln  Arg  Lys  Thr  Thr  Lys
               115                       120                        125

Glu  Ser  Leu  Ala  Gln  Thr  Ser  Ser  Thr  Ile  Thr  Glu  Ser  Leu  Met  Gly
          130                       135                       140

Ile  Ser  Arg  Met  Met  Ala  Gln  Gln  Val  Gln  Gln  Ser  Glu  Glu  Ala  Met
145                      150                       155                      160

Gln  Ser  Leu  Val  Thr  Ser  Ser  Arg  Thr  Ile  Leu  Asp  Ala  Asn  Glu  Glu
                    165                       170                        175

Phe  Lys  Ser  Met  Ser  Gly  Thr  Ile  Gln  Leu  Gly  Arg  Lys  Leu  Ile  Thr
                    180                       185                        190

Lys  Tyr  Asn  Arg  Arg  Glu  Leu  Thr  Asp  Lys  Leu  Leu  Ile  Phe  Leu  Ala
               195                       200                        205

Leu  Arg  Leu  Phe  Leu  Ala  Thr  Val  Leu  Tyr  Ile  Val  Lys  Lys  Arg  Leu
          210                       215                        220

Phe  Pro  Phe  Leu
225
```

( 2 ) INFORMATION FOR SEQ ID NO:22:

( i ) SEQUENCE CHARACTERISTICS:
    ( A ) LENGTH: 1386 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 214..1155

( x i ) SEQUENCE DESCRIPTION: SEQ ID NO:22:

```
CTGCGGCCGG GGGATTGGGC CGGGGTCTCC ACCGCCGACC GAGGGGAGCG GCGTCCGCTC        60

GGCCCTGCTT TTTGCGACCT GCCGTCAGCC CCACGTCGCC GGCCTGGAGG GGCGAAGAGG       120

ACGAGGGGCG ACGAAGGCCC AAGGCTTCCT CCGGGGACAT TGGCTCCCTG GATTATCAAG       180

CAGTTTGTAG TTGACATTGA ATCCAGGCTG AGG ATG GAA GGT GTG GAA CTT AAA       234
                                    Met Glu Gly Val Glu Leu Lys
                                        230                 235

GAA GAA TGG CAA GAT GAA GAT TTT CCG ATA CCT TTA CCA GAA GAT GAT        282
Glu Glu Trp Gln Asp Glu Asp Phe Pro Ile Pro Leu Pro Glu Asp Asp
            240                 245                 250

AGT ATT GAA GCA GAT ATA CTA GCT ATA ACT GGA CCA GAG GAC CAG CCT        330
Ser Ile Glu Ala Asp Ile Leu Ala Ile Thr Gly Pro Glu Asp Gln Pro
        255                 260                 265

GGC TCA CTA GAA GTT AAT GGA AAT AAA GTG AGA AAG AAA CTA ATG GCT        378
Gly Ser Leu Glu Val Asn Gly Asn Lys Val Arg Lys Lys Leu Met Ala
    270                 275                 280

CCA GAC ATT AGC CTG ACA CTG GAT CCT AGT GAT GGC TCT GTA TTG TCA        426
Pro Asp Ile Ser Leu Thr Leu Asp Pro Ser Asp Gly Ser Val Leu Ser
285                 290                 295

GAT GAT TTG GAT GAA AGT GGG GAG ATT GAC TTA GAT GGC TTA GAC ACA        474
Asp Asp Leu Asp Glu Ser Gly Glu Ile Asp Leu Asp Gly Leu Asp Thr
300                 305                 310                 315

CCG TCA GAG AAT AGT AAT GAG TTT GAG TGG GAA GAT GAT CTT CCA AAA        522
Pro Ser Glu Asn Ser Asn Glu Phe Glu Trp Glu Asp Asp Leu Pro Lys
                320                 325                 330

CCC AAG ACT ACT GAA GTA ATT AGG AAA GGC TCA ATT ACT GAA TAC ACA        570
Pro Lys Thr Thr Glu Val Ile Arg Lys Gly Ser Ile Thr Glu Tyr Thr
            335                 340                 345

GCA GCA GAG GAA AAA GAA GAT GGA CGA CGC TGG CGT ATG TTC AGG ATT        618
Ala Ala Glu Glu Lys Glu Asp Gly Arg Arg Trp Arg Met Phe Arg Ile
        350                 355                 360

GGA GAA CAG GAC CAC AGG GTT GAT ATG AAG GCA ATT GAA CCC TAT AAA        666
Gly Glu Gln Asp His Arg Val Asp Met Lys Ala Ile Glu Pro Tyr Lys
    365                 370                 375

AAA GTT ATC AGC CAT GGG GGA TAT TAT GGG GAT GGA TTA AAT GCC ATT        714
Lys Val Ile Ser His Gly Gly Tyr Tyr Gly Asp Gly Leu Asn Ala Ile
380                 385                 390                 395

GTT GTA TTT GCT GTC TGT TTC ATG CCT GAA AGT AGT CAG CCT AAC TAT        762
Val Val Phe Ala Val Cys Phe Met Pro Glu Ser Ser Gln Pro Asn Tyr
                400                 405                 410

AGA TAC CTG ATG GAC AAT CTT TTT AAA TAT GTT ATT GGC ACT TTG GAG        810
Arg Tyr Leu Met Asp Asn Leu Phe Lys Tyr Val Ile Gly Thr Leu Glu
            415                 420                 425

CTA TTA GTA GCA GAA AAC TAC ATG ATA GTT TAT TTA AAT GGT GCA ACA        858
Leu Leu Val Ala Glu Asn Tyr Met Ile Val Tyr Leu Asn Gly Ala Thr
        430                 435                 440

ACT CGA AGA AAA ATG CCC AGT CTG GGA TGG CTC AGG AAA TGT TAT CAG        906
Thr Arg Arg Lys Met Pro Ser Leu Gly Trp Leu Arg Lys Cys Tyr Gln
```

-continued

```
                    445                           450                           455
CAA  ATT  GAT  AGA  AGG  TTA  CGG  AAA  AAT  CTA  AAA  TCC  CTA  ATC  ATT  GTA         954
Gln  Ile  Asp  Arg  Arg  Leu  Arg  Lys  Asn  Leu  Lys  Ser  Leu  Ile  Ile  Val
460                 465                      470                      475

CAT  CCT  TCT  TGG  TTT  ATC  AGA  ACA  CTT  CTG  GCT  GTT  ACA  AGA  CCA  TTT        1002
His  Pro  Ser  Trp  Phe  Ile  Arg  Thr  Leu  Leu  Ala  Val  Thr  Arg  Pro  Phe
               480                      485                           490

ATT  AGC  TCG  AAA  TTC  AGC  CAA  AAA  ATT  AGA  TAC  GTG  TTT  AAT  TTG  GCA        1050
Ile  Ser  Ser  Lys  Phe  Ser  Gln  Lys  Ile  Arg  Tyr  Val  Phe  Asn  Leu  Ala
               495                      500                      505

GAA  CTA  GCA  GAA  CTT  GTC  CCC  ATG  GAA  TAC  GTT  GGC  ATA  CCA  GAA  TGC        1098
Glu  Leu  Ala  Glu  Leu  Val  Pro  Met  Glu  Tyr  Val  Gly  Ile  Pro  Glu  Cys
          510                      515                           520

ATA  AAA  CAA  GTT  GAT  CAA  GAA  CTT  AAT  GGA  AAA  CAA  GAT  GAA  CCG  AAA        1146
Ile  Lys  Gln  Val  Asp  Gln  Glu  Leu  Asn  Gly  Lys  Gln  Asp  Glu  Pro  Lys
     525                      530                      535

AAT  GAA  CAG  TAAGTTTGGC  ATCTAGTCCA  AACAAGACTG  AAGAATGTGC                          1195
Asn  Glu  Gln
540

TGATGGAGCA  GTGCTGTTTC  TGCATTCATA  ATGCATTTAT  TGGCCATATT  TTTATGTAAC                 1255

CTGTTACAAA  ATAGACTTGA  CTTTTTCATA  ATGGACTTTT  GTATTATACA  AGGGACTGTT                 1315

CACTGCTGTA  CTGGTTTGCA  AATTTCTTGA  ATTAGCTCT   TTATGCTAAC  TGTATTATTA                 1375

TCATTTTATA  T                                                                           1386
```

(2) INFORMATION FOR SEQ ID NO:23:

(i) SEQUENCE CHARACTERISTICS:
    (A) LENGTH: 314 amino acids
    (B) TYPE: amino acid
    (D) TOPOLOGY: linear (ii) MOLECULE TYPE: protein (xi) SEQUENCE DESCRIPTION: SEQ ID NO:23:

```
Met  Glu  Gly  Val  Glu  Leu  Lys  Glu  Glu  Trp  Gln  Asp  Glu  Asp  Phe  Pro
1                   5                        10                       15

Ile  Pro  Leu  Pro  Glu  Asp  Asp  Ser  Ile  Glu  Ala  Asp  Ile  Leu  Ala  Ile
               20                       25                       30

Thr  Gly  Pro  Glu  Asp  Gln  Pro  Gly  Ser  Leu  Glu  Val  Asn  Gly  Asn  Lys
          35                       40                       45

Val  Arg  Lys  Lys  Leu  Met  Ala  Pro  Asp  Ile  Ser  Leu  Thr  Leu  Asp  Pro
     50                       55                       60

Ser  Asp  Gly  Ser  Val  Leu  Ser  Asp  Asp  Leu  Asp  Glu  Ser  Gly  Glu  Ile
65                       70                       75                       80

Asp  Leu  Asp  Gly  Leu  Asp  Thr  Pro  Ser  Glu  Asn  Ser  Asn  Glu  Phe  Glu
                    85                       90                       95

Trp  Glu  Asp  Asp  Leu  Pro  Lys  Pro  Lys  Thr  Thr  Glu  Val  Ile  Arg  Lys
               100                      105                      110

Gly  Ser  Ile  Thr  Glu  Tyr  Thr  Ala  Ala  Glu  Glu  Lys  Glu  Asp  Gly  Arg
          115                      120                      125

Arg  Trp  Arg  Met  Phe  Arg  Ile  Gly  Glu  Gln  Asp  His  Arg  Val  Asp  Met
     130                      135                      140

Lys  Ala  Ile  Glu  Pro  Tyr  Lys  Lys  Val  Ile  Ser  His  Gly  Gly  Tyr  Tyr
145                      150                      155                      160

Gly  Asp  Gly  Leu  Asn  Ala  Ile  Val  Val  Phe  Ala  Val  Cys  Phe  Met  Pro
                    165                      170                      175

Glu  Ser  Ser  Gln  Pro  Asn  Tyr  Arg  Tyr  Leu  Met  Asp  Asn  Leu  Phe  Lys
```

```
                    1 8 0                     1 8 5                     1 9 0
Tyr  Val  Ile  Gly  Thr  Leu  Glu  Leu  Leu  Val  Ala  Glu  Asn  Tyr  Met  Ile
               1 9 5                     2 0 0                     2 0 5

Val  Tyr  Leu  Asn  Gly  Ala  Thr  Thr  Arg  Arg  Lys  Met  Pro  Ser  Leu  Gly
          2 1 0                     2 1 5                     2 2 0

Trp  Leu  Arg  Lys  Cys  Tyr  Gln  Gln  Ile  Asp  Arg  Arg  Leu  Arg  Lys  Asn
2 2 5                     2 3 0                     2 3 5                     2 4 0

Leu  Lys  Ser  Leu  Ile  Ile  Val  His  Pro  Ser  Trp  Phe  Ile  Arg  Thr  Leu
                    2 4 5                     2 5 0                     2 5 5

Leu  Ala  Val  Thr  Arg  Pro  Phe  Ile  Ser  Ser  Lys  Phe  Ser  Gln  Lys  Ile
               2 6 0                     2 6 5                     2 7 0

Arg  Tyr  Val  Phe  Asn  Leu  Ala  Glu  Leu  Ala  Glu  Leu  Val  Pro  Met  Glu
          2 7 5                     2 8 0                     2 8 5

Tyr  Val  Gly  Ile  Pro  Glu  Cys  Ile  Lys  Gln  Val  Asp  Gln  Glu  Leu  Asn
     2 9 0                     2 9 5                     3 0 0

Gly  Lys  Gln  Asp  Glu  Pro  Lys  Asn  Glu  Gln
3 0 5                     3 1 0
```

( 2 ) INFORMATION FOR SEQ ID NO:24:

( i ) SEQUENCE CHARACTERISTICS:
        ( A ) LENGTH: 826 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 109..690

( x i ) SEQUENCE DESCRIPTION: SEQ ID NO:24:

```
AAAGAGATCT  GGAATTCGGA  TCCTCGAGGC  CACGAAGGCC  ACCGCCCGCA  GCTGAAGCAC          6 0

ATCCGCAGCC  CGGCGCGACT  CCGATCGCCG  CAGTTGCCCT  CTGGCGCC ATG  TCC  GAG         1 1 7
                                                        Met  Ser  Glu
                                                        3 1 5

AAC  GGA  GCG  CCC  GGG  ATG  CAG  GAG  GAG  AGC  CTG  CAG  GGC  TCC  TGG  GTA  1 6 5
Asn  Gly  Ala  Pro  Gly  Met  Gln  Glu  Glu  Ser  Leu  Gln  Gly  Ser  Trp  Val
          3 2 0                     3 2 5                     3 3 0

GAA  CTG  CAC  TTC  AGC  AAT  AAT  GGG  AAC  GGG  GGC  AGC  GTT  CCA  GCC  TCG  2 1 3
Glu  Leu  His  Phe  Ser  Asn  Asn  Gly  Asn  Gly  Gly  Ser  Val  Pro  Ala  Ser
     3 3 5                     3 4 0                     3 4 5

GTT  TCT  ATT  TAT  AAT  GGA  GAC  ATG  GAA  AAA  ATA  CTG  CTG  GAC  GCA  CAG  2 6 1
Val  Ser  Ile  Tyr  Asn  Gly  Asp  Met  Glu  Lys  Ile  Leu  Leu  Asp  Ala  Gln
3 5 0                     3 5 5                     3 6 0                     3 6 5

CAT  GAG  TCT  GGA  CGG  AGT  AGC  TCC  AAG  AGC  TCT  CAC  TGT  GAC  AGC  CCA  3 0 9
His  Glu  Ser  Gly  Arg  Ser  Ser  Ser  Lys  Ser  Ser  His  Cys  Asp  Ser  Pro
                    3 7 0                     3 7 5                     3 8 0

CCT  CGC  TCG  CAG  ACA  CCA  CAA  GAT  ACC  AAC  AGG  GCT  TCT  GAA  ACA  GAT  3 5 7
Pro  Arg  Ser  Gln  Thr  Pro  Gln  Asp  Thr  Asn  Arg  Ala  Ser  Glu  Thr  Asp
               3 8 5                     3 9 0                     3 9 5

ACC  CAT  AGC  ATT  GGA  GAG  AAA  AAC  AGC  TCA  CAG  TCT  GAG  GAA  GAT  GAT  4 0 5
Thr  His  Ser  Ile  Gly  Glu  Lys  Asn  Ser  Ser  Gln  Ser  Glu  Glu  Asp  Asp
          4 0 0                     4 0 5                     4 1 0

ATT  GAA  AGA  AGG  AAA  GAA  GTT  GAA  AGC  ATC  TTG  AAG  AAA  AAC  TCA  GAT  4 5 3
Ile  Glu  Arg  Arg  Lys  Glu  Val  Glu  Ser  Ile  Leu  Lys  Lys  Asn  Ser  Asp
     4 1 5                     4 2 0                     4 2 5

TGG  ATA  TGG  GAT  TGG  TCA  AGT  CGG  CCG  GAA  AAT  ATT  CCC  CCC  AAG  GAG  5 0 1
Trp  Ile  Trp  Asp  Trp  Ser  Ser  Arg  Pro  Glu  Asn  Ile  Pro  Pro  Lys  Glu
4 3 0                     4 3 5                     4 4 0                     4 4 5
```

```
TTC  CTC  TTT  AAA  CAC  CCG  AAG  CGC  ACG  GCC  ACC  CTC  AGC  ATG  AGG  AAC       549
Phe  Leu  Phe  Lys  His  Pro  Lys  Arg  Thr  Ala  Thr  Leu  Ser  Met  Arg  Asn
               450                      455                     460

ACG  AGC  GTC  ATG  AAG  AAA  GGG  GGC  ATA  TTC  TCT  GCA  GAA  TTT  CTG  AAA       597
Thr  Ser  Val  Met  Lys  Lys  Gly  Gly  Ile  Phe  Ser  Ala  Glu  Phe  Leu  Lys
               465                      470                     475

GTT  TTC  CTT  CCA  TCT  CTG  CTG  CTC  TCT  CAT  TTG  CTG  GCC  ATC  GGA  TTG       645
Val  Phe  Leu  Pro  Ser  Leu  Leu  Leu  Ser  His  Leu  Leu  Ala  Ile  Gly  Leu
               480                      485                     490

GGG  ATC  TAT  ATT  GGA  AGG  CGT  CTG  ACA  ACC  TCC  ACC  AGC  ACC  TTT            690
Gly  Ile  Tyr  Ile  Gly  Arg  Arg  Leu  Thr  Thr  Ser  Thr  Ser  Thr  Phe
          495                      500                     505

TGATGAAGAA  CTGGAGTCTG  ACTTGGTTCG  TTAGTGGATT  ACTTCTGAGC  TTGCAACATA               750

GCTCACTGAA  GAGCTGTTAG  ATCCTGGGCC  TTCGTGGCTC  GAGAGACTAG  AATCGCAGAT               810

ACGAAAACCC  CGCAGC                                                                   826
```

( 2 ) INFORMATION FOR SEQ ID NO:25:

( i ) SEQUENCE CHARACTERISTICS:
        ( A ) LENGTH: 194 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Met  Ser  Glu  Asn  Gly  Ala  Pro  Gly  Met  Gln  Glu  Glu  Ser  Leu  Gln  Gly
 1                  5                        10                      15

Ser  Trp  Val  Glu  Leu  His  Phe  Ser  Asn  Asn  Gly  Asn  Gly  Ser  Val
               20                      25                      30

Pro  Ala  Ser  Val  Ser  Ile  Tyr  Asn  Gly  Asp  Met  Glu  Lys  Ile  Leu  Leu
               35                      40                      45

Asp  Ala  Gln  His  Glu  Ser  Gly  Arg  Ser  Ser  Ser  Lys  Ser  Ser  His  Cys
          50                      55                      60

Asp  Ser  Pro  Pro  Arg  Ser  Gln  Thr  Pro  Gln  Asp  Thr  Asn  Arg  Ala  Ser
 65                     70                      75                      80

Glu  Thr  Asp  Thr  His  Ser  Ile  Gly  Glu  Lys  Asn  Ser  Ser  Gln  Ser  Glu
               85                      90                      95

Glu  Asp  Asp  Ile  Glu  Arg  Arg  Lys  Glu  Val  Glu  Ser  Ile  Leu  Lys  Lys
               100                     105                     110

Asn  Ser  Asp  Trp  Ile  Trp  Asp  Trp  Ser  Ser  Arg  Pro  Glu  Asn  Ile  Pro
          115                     120                     125

Pro  Lys  Glu  Phe  Leu  Phe  Lys  His  Pro  Lys  Arg  Thr  Ala  Thr  Leu  Ser
     130                     135                     140

Met  Arg  Asn  Thr  Ser  Val  Met  Lys  Lys  Gly  Gly  Ile  Phe  Ser  Ala  Glu
145                      150                     155                     160

Phe  Leu  Lys  Val  Phe  Leu  Pro  Ser  Leu  Leu  Leu  Ser  His  Leu  Leu  Ala
               165                     170                     175

Ile  Gly  Leu  Gly  Ile  Tyr  Ile  Gly  Arg  Arg  Leu  Thr  Thr  Ser  Thr  Ser
               180                     185                     190

Thr  Phe
```

( 2 ) INFORMATION FOR SEQ ID NO:26:

( i ) SEQUENCE CHARACTERISTICS:
        ( A ) LENGTH: 946 base pairs
        ( B ) TYPE: nucleic acid
        ( C ) STRANDEDNESS: single -continued ( D ) TOPOLOGY: linear ( i i ) MOLECULE TYPE: cDNA ( i x ) FEATURE:
    ( A ) NAME/KEY: CDS
    ( B ) LOCATION: 26..505

( x i ) SEQUENCE DESCRIPTION: SEQ ID NO:26:

```
CAGCATCGCC GCCGCCAGAG GAGAA ATG TCT GAA GTA AGA CCC CTC TCC AGA        52
                            Met Ser Glu Val Arg Pro Leu Ser Arg
                            195             200

GAC ATC TTG ATG GAG ACC CTC CTG TAT GAG CAG CTC CTG GAA CCC CCG       100
Asp Ile Leu Met Glu Thr Leu Leu Tyr Glu Gln Leu Leu Glu Pro Pro
    205             210             215

ACC ATG GAG GTT CTT GGC ATG ACT GAC TCT GAA GAG GAC CTG GAC CCT       148
Thr Met Glu Val Leu Gly Met Thr Asp Ser Glu Glu Asp Leu Asp Pro
220             225             230             235

ATG GAG GAC TTC GAT TCT TTG GAA TGC ATG GAG GGC AGT GAC GCA TTG       196
Met Glu Asp Phe Asp Ser Leu Glu Cys Met Glu Gly Ser Asp Ala Leu
                240             245             250

GCC CTG CGG CTG GCC TGC ATC GGG GAC GAG ATG GAC GTG AGC CTC AGG       244
Ala Leu Arg Leu Ala Cys Ile Gly Asp Glu Met Asp Val Ser Leu Arg
            255             260             265

GCC CCG CGC CTG GCC CAG CTC TCC GAG GTG GCC ATG CAC AGC CTG GGT       292
Ala Pro Arg Leu Ala Gln Leu Ser Glu Val Ala Met His Ser Leu Gly
        270             275             280

CTG GCT TTC ATC TAC GAC CAG ACT GAG GAC ATC AGG GAT GTT CTT AGA       340
Leu Ala Phe Ile Tyr Asp Gln Thr Glu Asp Ile Arg Asp Val Leu Arg
    285             290             295

AGT TTC ATG GAC GGT TTC ACC ACA CTT AAG GAG AAC ATA ATG AGG TTC       388
Ser Phe Met Asp Gly Phe Thr Thr Leu Lys Glu Asn Ile Met Arg Phe
300             305             310             315

TGG AGA TCC CCG AAC CCC GGG TCC TGG GTG TCC TGC GAA CAG GTG CTG       436
Trp Arg Ser Pro Asn Pro Gly Ser Trp Val Ser Cys Glu Gln Val Leu
                320             325             330

CTG GCG CTG CTG CTG CTG GCG CTG CTG CTG CCG CTG CTC AGC GGG           484
Leu Ala Leu Leu Leu Leu Leu Ala Leu Leu Leu Pro Leu Leu Ser Gly
            335             340             345

GGC CTG CAC CTG CTG CTC AAG TGAGGCCCCG GCGGCTCAGG GCGTGGCTGG          535
Gly Leu His Leu Leu Leu Lys
        350

CCCCACCCCC ATGACCACTG CCCTGGAGGT GGCGGCCTGC TGCTGTTATC TTTTTAACTG     595

TTTTCTCATG ATGCCTTTTT ATATTTAAAC CCCGAGATAG TGCTGGAACA CTGCTGAGGT     655

TTTATACTCA GGTTTTTTGT TTTTTTTTA TTCCAGTTTT CGTTTTTCT AAAAGATGAA       715

TTCCTATGGC TCTGCAATTG TCACCGGTTA ACTGTGGCCT GTGCCCAGGA AGAGCCATTC     775

ACTCCTGCCC CTGCCCACAC GGCAGGTAGC AGGGGGAGTG CTGGTCACAC CCCTGTGTGA     835

TATGTGATGC CCTCGGCAAA GAATCTACTG GAATAGATTC CGAGGAGCAG GAGTGCTCAA     895

TAAAATGTTG GTTTCCAGCA AAAAAAAAA AAAGGCCTTC GTGGCCTCGA G               946
```

( 2 ) INFORMATION FOR SEQ ID NO:27:

( i ) SEQUENCE CHARACTERISTICS:
        ( A ) LENGTH: 160 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
Met  Ser  Glu  Val  Arg  Pro  Leu  Ser  Arg  Asp  Ile  Leu  Met  Glu  Thr  Leu
 1              5                        10                      15

Leu  Tyr  Glu  Gln  Leu  Leu  Glu  Pro  Pro  Thr  Met  Glu  Val  Leu  Gly  Met
               20                       25                     30

Thr  Asp  Ser  Glu  Glu  Asp  Leu  Asp  Pro  Met  Glu  Asp  Phe  Asp  Ser  Leu
          35                       40                      45

Glu  Cys  Met  Glu  Gly  Ser  Asp  Ala  Leu  Ala  Leu  Arg  Leu  Ala  Cys  Ile
     50                       55                      60

Gly  Asp  Glu  Met  Asp  Val  Ser  Leu  Arg  Ala  Pro  Arg  Leu  Ala  Gln  Leu
 65                  70                       75                            80

Ser  Glu  Val  Ala  Met  His  Ser  Leu  Gly  Leu  Ala  Phe  Ile  Tyr  Asp  Gln
                85                       90                            95

Thr  Glu  Asp  Ile  Arg  Asp  Val  Leu  Arg  Ser  Phe  Met  Asp  Gly  Phe  Thr
               100                      105                     110

Thr  Leu  Lys  Glu  Asn  Ile  Met  Arg  Phe  Trp  Arg  Ser  Pro  Asn  Pro  Gly
          115                      120                     125

Ser  Trp  Val  Ser  Cys  Glu  Gln  Val  Leu  Leu  Ala  Leu  Leu  Leu  Leu  Leu
     130                      135                     140

Ala  Leu  Leu  Leu  Pro  Leu  Ser  Gly  Gly  Leu  His  Leu  Leu  Leu  Lys
145                      150                     155                       160
```

( 2 ) INFORMATION FOR SEQ ID NO:28:

( i ) SEQUENCE CHARACTERISTICS:
        ( A ) LENGTH: 981 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..777

( x i ) SEQUENCE DESCRIPTION: SEQ ID NO:28:

```
ATG  GAC  GCC  TGG  GTC  CGC  TTC  AGT  GCT  CAG  AGC  CAA  GCC  CGG  GAG  CGG      48
Met  Asp  Ala  Trp  Val  Arg  Phe  Ser  Ala  Gln  Ser  Gln  Ala  Arg  Glu  Arg
               165                      170                     175

CTG  TGT  AGG  GCC  GCC  CAG  TAT  GCT  TGC  TCT  CTT  CTT  GGC  CAT  GCG  CTG      96
Leu  Cys  Arg  Ala  Ala  Gln  Tyr  Ala  Cys  Ser  Leu  Leu  Gly  His  Ala  Leu
               180                      185                     190

CAG  AGG  CAT  GGA  GCC  AGT  CCT  GAG  TTA  CAG  AAA  CAG  ATT  CGA  CAA  CTG     144
Gln  Arg  His  Gly  Ala  Ser  Pro  Glu  Leu  Gln  Lys  Gln  Ile  Arg  Gln  Leu
          195                      200                     205

GAG  AGC  CAC  CTG  AGC  CTT  GGA  AGA  AAG  CTT  CTA  CGC  CTG  GGT  AAC  TCA     192
Glu  Ser  His  Leu  Ser  Leu  Gly  Arg  Lys  Leu  Leu  Arg  Leu  Gly  Asn  Ser
          210                      215                     220

GCA  GAT  GCC  CTT  GAG  TCA  GCC  AAA  AGA  GCT  GTT  CAC  CTA  TCA  GAT  GTT     240
Ala  Asp  Ala  Leu  Glu  Ser  Ala  Lys  Arg  Ala  Val  His  Leu  Ser  Asp  Val
225                      230                     235                       240

GTC  CTG  AGA  TTC  TGC  ATC  ACT  GTT  AGT  CAC  CTC  AAT  CGA  GCC  TTG  TAC     288
Val  Leu  Arg  Phe  Cys  Ile  Thr  Val  Ser  His  Leu  Asn  Arg  Ala  Leu  Tyr
                    245                      250                     255

TTC  GCC  TGT  CAC  AAT  GTC  CTG  TGG  GCT  GGA  AAG  TCT  GGA  CTG  GCT  CCC     336
Phe  Ala  Cys  His  Asn  Val  Leu  Trp  Ala  Gly  Lys  Ser  Gly  Leu  Ala  Pro
               260                      265                     270

CGT  GTG  GAT  CAG  GAG  AAG  TGG  GCC  CAG  CGT  TCA  TTC  AGG  TAC  TAT  TTG     384
Arg  Val  Asp  Gln  Glu  Lys  Trp  Ala  Gln  Arg  Ser  Phe  Arg  Tyr  Tyr  Leu
               275                      280                     285

TTT  TCC  CTC  ATC  ATG  AAT  TTG  AGC  CGT  GAT  GCT  TAT  GAG  ATT  CGC  CTA     432
```

|     |     |     |     |     |     |     |     |     |     |     |     |     |     |     |     |     |
|---|---|---|---|---|---|---|---|---|---|---|---|---|---|---|---|---|
| Phe | Ser | Leu | Ile | Met | Asn | Leu | Ser | Arg | Asp | Ala | Tyr | Glu | Ile | Arg | Leu | |
|     |     |     |     | 290 |     |     | 295 |     |     |     | 300 |     |     |     |     | |

```
CTG ATG GAG CAA GAG TCT TCT GCT TGT AGC CGG CGA CTG AAA GGT TCT       480
Leu Met Glu Gln Glu Ser Ser Ala Cys Ser Arg Arg Leu Lys Gly Ser
305             310             315             320

GGA GGA GGA GTC CCA GGA GGA AGT GAA ACT GGG GGA CTT GGG GGA CCA       528
Gly Gly Gly Val Pro Gly Gly Ser Glu Thr Gly Gly Leu Gly Gly Pro
            325             330             335

GGG ACT CCA GGA GGA GGT CTG CCC CAA CTG GCT CTG AAA CTT CGG CTG       576
Gly Thr Pro Gly Gly Gly Leu Pro Gln Leu Ala Leu Lys Leu Arg Leu
        340             345             350

CAA GTC CTG CTC CTG GCT CGA GTC CTT AGA GGT CAT CCC CCA CTT CTG       624
Gln Val Leu Leu Leu Ala Arg Val Leu Arg Gly His Pro Pro Leu Leu
        355             360             365

CTA GAC GTG GTC AGA AAT GCC TGT GAT CTC TTC ATT CCT CTG GAC AAA       672
Leu Asp Val Val Arg Asn Ala Cys Asp Leu Phe Ile Pro Leu Asp Lys
370             375             380

CTA GCG CTC TGG CGC TGT GGC CCT GGG ATT GTG GGG CTT TGT GGC CTC       720
Leu Ala Leu Trp Arg Cys Gly Pro Gly Ile Val Gly Leu Cys Gly Leu
385             390             395             400

GTG TCC TCC ATC CTG TCT ATT CTC ACC CTA ATC TAT CCC TGG CTA CGA       768
Val Ser Ser Ile Leu Ser Ile Leu Thr Leu Ile Tyr Pro Trp Leu Arg
            405             410             415

CTC AAG CCC TGACTTCCGG TACAGGATAA GGAGGGGACC TGAATTGGTG              817
Leu Lys Pro

AGATGGAATC TTAGATCGTC CCCATGTGCC AGCCTCATTC GAATTCTACT CTTTGGTTAA   877

AGTTAGAAAT TCAGAGATTT AGGGGTGGAG GAGGAAGAGC TTTGGGGAAG ATGAGGTAAG   937

GAAAGATGAC TCGTGAAGTT AATAGGATGT CTCTAATTTC TAGA                    981
```

( 2 ) INFORMATION FOR SEQ ID NO:29:

( i ) SEQUENCE CHARACTERISTICS:
        ( A ) LENGTH: 259 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Met Asp Ala Trp Val Arg Phe Ser Ala Gln Ser Gln Ala Arg Glu Arg
1               5                   10                  15

Leu Cys Arg Ala Ala Gln Tyr Ala Cys Ser Leu Leu Gly His Ala Leu
            20                  25                  30

Gln Arg His Gly Ala Ser Pro Glu Leu Gln Lys Gln Ile Arg Gln Leu
        35                  40                  45

Glu Ser His Leu Ser Leu Gly Arg Lys Leu Leu Arg Leu Gly Asn Ser
    50                  55                  60

Ala Asp Ala Leu Glu Ser Ala Lys Arg Ala Val His Leu Ser Asp Val
65                  70                  75                  80

Val Leu Arg Phe Cys Ile Thr Val Ser His Leu Asn Arg Ala Leu Tyr
                85                  90                  95

Phe Ala Cys His Asn Val Leu Trp Ala Gly Lys Ser Gly Leu Ala Pro
            100                 105                 110

Arg Val Asp Gln Glu Lys Trp Ala Gln Arg Ser Phe Arg Tyr Tyr Leu
        115                 120                 125

Phe Ser Leu Ile Met Asn Leu Ser Arg Asp Ala Tyr Glu Ile Arg Leu
    130                 135                 140

Leu Met Glu Gln Glu Ser Ser Ala Cys Ser Arg Arg Leu Lys Gly Ser
```

|     |     |     |     |     | 145 |     |     |     |     | 150 |     |     |     |     | 155 |     |     |     |     | 160 |
|-----|-----|-----|-----|-----|-----|-----|-----|-----|-----|-----|-----|-----|-----|-----|-----|-----|-----|-----|-----|-----|

Gly Gly Gly Val Pro Gly Gly Ser Glu Thr Gly Gly Leu Gly Gly Pro
            165                 170                 175

Gly Thr Pro Gly Gly Gly Leu Pro Gln Leu Ala Leu Lys Leu Arg Leu
            180                 185                 190

Gln Val Leu Leu Leu Ala Arg Val Leu Arg Gly His Pro Pro Leu Leu
            195                 200                 205

Leu Asp Val Val Arg Asn Ala Cys Asp Leu Phe Ile Pro Leu Asp Lys
    210                 215                 220

Leu Ala Leu Trp Arg Cys Gly Pro Gly Ile Val Gly Leu Cys Gly Leu
225                 230                 235                 240

Val Ser Ser Ile Leu Ser Ile Leu Thr Leu Ile Tyr Pro Trp Leu Arg
                245                 250                 255

Leu Lys Pro (2) INFORMATION FOR SEQ ID NO:30:

(i) SEQUENCE CHARACTERISTICS:
        (A) LENGTH: 2166 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1503

(xi) SEQUENCE DESCRIPTION: SEQ ID NO:30:

AGT CAA GTC GAG TTT CTT TGC ATG TCA CTG GCC AAT CCT CTT CCA ACA   48
Ser Gln Val Glu Phe Leu Cys Met Ser Leu Ala Asn Pro Leu Pro Thr
260                 265                 270                 275

AAT TAC ACG TGG TAC CAC AAT GGG AAA GAA ATG CAG GGA AGG ACA GAG   96
Asn Tyr Thr Trp Tyr His Asn Gly Lys Glu Met Gln Gly Arg Thr Glu
                280                 285                 290

GAG AAA GTC CAC ATC CCA AAG ATC CTC CCC TGG CAC GCT GGG ACT TAT  144
Glu Lys Val His Ile Pro Lys Ile Leu Pro Trp His Ala Gly Thr Tyr
            295                 300                 305

TCC TGT GTG GCA GAA AAC ATT CTT GGT ACT GGA CAG AGG GGC CCG GGA  192
Ser Cys Val Ala Glu Asn Ile Leu Gly Thr Gly Gln Arg Gly Pro Gly
            310                 315                 320

GCT GAG CTG GAT GTC CAG TAT CCT CCC AAG AAG GTG ACC ACA GTG ATT  240
Ala Glu Leu Asp Val Gln Tyr Pro Pro Lys Lys Val Thr Thr Val Ile
        325                 330                 335

CAA AAC CCC ATG CCG ATT CGA GAA GGA GAC ACA GTG ACC CTT TCC TGT  288
Gln Asn Pro Met Pro Ile Arg Glu Gly Asp Thr Val Thr Leu Ser Cys
340                 345                 350                 355

AAC TAC AAT TCC AGT AAC CCC AGT GTT ACC CGG TAT GAA TGG AAA CCC  336
Asn Tyr Asn Ser Ser Asn Pro Ser Val Thr Arg Tyr Glu Trp Lys Pro
                360                 365                 370

CAT GGC GCC TGG GAG GAG CCA TCG CTT GGG GTG CTG AAG ATC CAA AAC  384
His Gly Ala Trp Glu Glu Pro Ser Leu Gly Val Leu Lys Ile Gln Asn
            375                 380                 385

GTT GGC TGG GAC AAC ACA ACC ATC GCC TGC GCA CGT TGT AAT AGT TGG  432
Val Gly Trp Asp Asn Thr Thr Ile Ala Cys Ala Arg Cys Asn Ser Trp
        390                 395                 400

TGC TCG TGG GCC TCC CCT GTC GCC CTG AAT GTC CAG TAT GCC CCC CGA  480
Cys Ser Trp Ala Ser Pro Val Ala Leu Asn Val Gln Tyr Ala Pro Arg
    405                 410                 415

GAC GTG AGG GTC CGG AAA ATC AAG CCC CTT TCC GAG ATT CAC TCT GGA  528

-continued

| | | | | | | | | | | | | | | | |
|---|---|---|---|---|---|---|---|---|---|---|---|---|---|---|---|
| Asp | Val | Arg | Val | Arg | Lys | Ile | Lys | Pro | Leu | Ser | Glu | Ile | His | Ser | Gly |
| 420 | | | | 425 | | | | 430 | | | | | | | 435 |

| AAC | TCG | GTC | AGC | CTC | CAA | TGT | GAC | TTC | TCA | AGC | AGC | CAC | CCC | AAA | GAA | 576 |
|---|---|---|---|---|---|---|---|---|---|---|---|---|---|---|---|---|
| Asn | Ser | Val | Ser | Leu | Gln | Cys | Asp | Phe | Ser | Ser | Ser | His | Pro | Lys | Glu | |
| | | | | 440 | | | | 445 | | | | | | 450 | | |

| GTC | CAG | TTC | TTC | TGG | GAG | AAA | AAT | GGC | AGG | CTT | CTG | GGG | AAA | GAA | AGC | 624 |
|---|---|---|---|---|---|---|---|---|---|---|---|---|---|---|---|---|
| Val | Gln | Phe | Phe | Trp | Glu | Lys | Asn | Gly | Arg | Leu | Leu | Gly | Lys | Glu | Ser | |
| | | | 455 | | | | 460 | | | | | 465 | | | | |

| CAG | CTG | AAT | TTT | GAC | TCC | ATC | TCC | CCA | GAA | GAT | GCT | GGG | AGT | TAC | AGC | 672 |
|---|---|---|---|---|---|---|---|---|---|---|---|---|---|---|---|---|
| Gln | Leu | Asn | Phe | Asp | Ser | Ile | Ser | Pro | Glu | Asp | Ala | Gly | Ser | Tyr | Ser | |
| | | 470 | | | | 475 | | | | | 480 | | | | | |

| TGC | TGG | GTG | AAC | AAC | TCC | ATA | GGA | CAG | ACA | GCG | TCC | AAG | GCC | TGG | ACA | 720 |
|---|---|---|---|---|---|---|---|---|---|---|---|---|---|---|---|---|
| Cys | Trp | Val | Asn | Asn | Ser | Ile | Gly | Gln | Thr | Ala | Ser | Lys | Ala | Trp | Thr | |
| 485 | | | | | 490 | | | | | 495 | | | | | | |

| CTT | GAA | GTG | CTG | TAT | GCA | CCC | AGG | AGG | CTG | CGT | GTG | TCC | ATG | AGC | CCG | 768 |
|---|---|---|---|---|---|---|---|---|---|---|---|---|---|---|---|---|
| Leu | Glu | Val | Leu | Tyr | Ala | Pro | Arg | Arg | Leu | Arg | Val | Ser | Met | Ser | Pro | |
| 500 | | | | | 505 | | | | | 510 | | | | | 515 | |

| GGG | GAC | CAA | GTG | ATG | GAG | GGG | AAG | AGT | GCA | ACC | CTG | ACC | TGT | GAG | AGT | 816 |
|---|---|---|---|---|---|---|---|---|---|---|---|---|---|---|---|---|
| Gly | Asp | Gln | Val | Met | Glu | Gly | Lys | Ser | Ala | Thr | Leu | Thr | Cys | Glu | Ser | |
| | | | | 520 | | | | 525 | | | | | | 530 | | |

| GAC | GCC | AAC | CCT | CCC | GTC | TCC | CAC | TAC | ACC | TGG | TTT | GAC | TGG | AAT | AAC | 864 |
|---|---|---|---|---|---|---|---|---|---|---|---|---|---|---|---|---|
| Asp | Ala | Asn | Pro | Pro | Val | Ser | His | Tyr | Thr | Trp | Phe | Asp | Trp | Asn | Asn | |
| | | | 535 | | | | 540 | | | | | 545 | | | | |

| CAA | AGC | CTC | CCC | CAC | CAC | AGC | CAG | AAG | CTG | AGA | TTG | GAG | CCG | GTG | AAG | 912 |
|---|---|---|---|---|---|---|---|---|---|---|---|---|---|---|---|---|
| Gln | Ser | Leu | Pro | His | His | Ser | Gln | Lys | Leu | Arg | Leu | Glu | Pro | Val | Lys | |
| | 550 | | | | | 555 | | | | | 560 | | | | | |

| GTC | CAG | CAC | TCG | GGT | GCC | TAC | TGG | TGC | CAG | GGG | ACC | AAC | AGT | GTG | GGC | 960 |
|---|---|---|---|---|---|---|---|---|---|---|---|---|---|---|---|---|
| Val | Gln | His | Ser | Gly | Ala | Tyr | Trp | Cys | Gln | Gly | Thr | Asn | Ser | Val | Gly | |
| | 565 | | | | | 570 | | | | | 575 | | | | | |

| AAG | GGC | CGT | TCG | CCT | CTC | AGC | ACC | CTT | ACT | GTC | TAC | TAT | AGC | CCG | GAG | 1008 |
|---|---|---|---|---|---|---|---|---|---|---|---|---|---|---|---|---|
| Lys | Gly | Arg | Ser | Pro | Leu | Ser | Thr | Leu | Thr | Val | Tyr | Tyr | Ser | Pro | Glu | |
| 580 | | | | | 585 | | | | | 590 | | | | | 595 | |

| ACC | ATC | GGC | AGG | CGA | GTG | GCT | GTG | GGA | CTC | GGG | TCC | TGC | CTC | GCC | ATC | 1056 |
|---|---|---|---|---|---|---|---|---|---|---|---|---|---|---|---|---|
| Thr | Ile | Gly | Arg | Arg | Val | Ala | Val | Gly | Leu | Gly | Ser | Cys | Leu | Ala | Ile | |
| | | | | 600 | | | | | 605 | | | | | 610 | | |

| CTC | ATC | CTG | GCA | ATC | TGT | GGG | CTC | AAG | CTC | CAG | CGA | CGT | TGG | AAG | AGG | 1104 |
|---|---|---|---|---|---|---|---|---|---|---|---|---|---|---|---|---|
| Leu | Ile | Leu | Ala | Ile | Cys | Gly | Leu | Lys | Leu | Gln | Arg | Arg | Trp | Lys | Arg | |
| | | | | 615 | | | | 620 | | | | | 625 | | | |

| ACA | CAG | AGC | CAG | CAG | GGG | CTT | CAG | GAG | AAT | TCC | AGC | GGC | CAG | AGC | TTC | 1152 |
|---|---|---|---|---|---|---|---|---|---|---|---|---|---|---|---|---|
| Thr | Gln | Ser | Gln | Gln | Gly | Leu | Gln | Glu | Asn | Ser | Ser | Gly | Gln | Ser | Phe | |
| | | 630 | | | | | 635 | | | | | 640 | | | | |

| TTT | GTG | AGG | AAT | AAA | AAG | GTT | AGA | AGG | GCC | CCC | CTC | TCT | GAA | GGC | CCC | 1200 |
|---|---|---|---|---|---|---|---|---|---|---|---|---|---|---|---|---|
| Phe | Val | Arg | Asn | Lys | Lys | Val | Arg | Arg | Ala | Pro | Leu | Ser | Glu | Gly | Pro | |
| | 645 | | | | | 650 | | | | | 655 | | | | | |

| CAC | TCC | CTG | GGA | TGC | TAC | AAT | CCA | ATG | ATG | GAA | GAT | GGC | ATT | AGC | TAC | 1248 |
|---|---|---|---|---|---|---|---|---|---|---|---|---|---|---|---|---|
| His | Ser | Leu | Gly | Cys | Tyr | Asn | Pro | Met | Met | Glu | Asp | Gly | Ile | Ser | Tyr | |
| 660 | | | | | 665 | | | | | 670 | | | | | 675 | |

| ACC | ACC | CTG | CGC | TTT | CCC | GAG | ATG | AAC | ATA | CCA | CGA | ACT | GGA | GAT | GCA | 1296 |
|---|---|---|---|---|---|---|---|---|---|---|---|---|---|---|---|---|
| Thr | Thr | Leu | Arg | Phe | Pro | Glu | Met | Asn | Ile | Pro | Arg | Thr | Gly | Asp | Ala | |
| | | | | 680 | | | | | 685 | | | | | 690 | | |

| GAG | TCC | TCA | GAG | ATG | CAG | AGA | CCT | CCC | CGG | ACC | TGC | GAT | GAC | ACG | GTC | 1344 |
|---|---|---|---|---|---|---|---|---|---|---|---|---|---|---|---|---|
| Glu | Ser | Ser | Glu | Met | Gln | Arg | Pro | Pro | Arg | Thr | Cys | Asp | Asp | Thr | Val | |
| | | | | 695 | | | | | 700 | | | | | 705 | | |

| ACT | TAT | TCA | GCA | TTG | CAC | AAG | CGC | CAA | GTG | GGC | GAC | TAT | GAG | AAC | GTC | 1392 |
|---|---|---|---|---|---|---|---|---|---|---|---|---|---|---|---|---|
| Thr | Tyr | Ser | Ala | Leu | His | Lys | Arg | Gln | Val | Gly | Asp | Tyr | Glu | Asn | Val | |
| | | 710 | | | | | 715 | | | | | 720 | | | | |

| ATT | CCA | GAT | TTT | CCA | GAA | GAT | GAG | GGG | ATT | CAT | TAC | TCA | GAG | CTG | ATC | 1440 |
|---|---|---|---|---|---|---|---|---|---|---|---|---|---|---|---|---|
| Ile | Pro | Asp | Phe | Pro | Glu | Asp | Glu | Gly | Ile | His | Tyr | Ser | Glu | Leu | Ile | |
| | 725 | | | | | 730 | | | | | 735 | | | | | |

| CAG | TTT | GGG | GTC | GGG | GAG | CGG | CCT | CAG | GCA | CAA | GAA | AAT | GTG | GAC | TAT | 1488 |

| | | | | | | | | | | | | | | | |
|---|---|---|---|---|---|---|---|---|---|---|---|---|---|---|---|
|Gln|Phe|Gly|Val|Gly|Glu|Arg|Pro|Gln|Ala|Gln|Glu|Asn|Val|Asp|Tyr|
|740| | | | |745| | | |750| | | | |755| |

GTG ATC CTC AAA CAT TGACACTGGA TGGGCTGCAG CAGAGGCACT GGGGGCAGCG 1543
Val Ile Leu Lys His
                760

GGGGCCAGGG AAGTCCCCGA GTTTCCCCAG ACACCGCCAC ATGGCTTCCT CCTGCGTGCA 1603
TGTGCGCACA CACACACACA CACGCACACA CACACACACA CACTCACTGC GGAGAACCTT 1663
GTGCCTGGCT CAGAGCCAGT CTTTTGGTG AGGGTAACCC CAAACCTCCA AAACTCCTGC 1723
CCCTGTTCTC TTCCACTCTC CTTGCTACCC AGAAATCATC TAAATACCTG CCCTGACATG 1783
CACACCTCCC CTGCCCCACC AGCCCACTGG CCATCTCCAC CCGGAGCTGC TGTGTCCTCT 1843
GGATCTGCTC GTCATTTTCC TTCCCTTCTC CATCTCTCTG GCCCTCTACC CCTGATCTGA 1903
CATCCCCACT CACGAATATT ATGCCCAGTT TCTGCCTCTG AGGGAAAGCC CAGAAAGGA 1963
CAGAAACGAA GTAGAAAGGG GCCCAGTCCT GGCCTGGCTT CTCCTTTGGA AGTGAGGCAT 2023
TGCACGGGGA GACGTACGTA TCAGCGGCCC CTTGACTCTG GGGACTCCGG GTTTGAGATG 2083
GACACACTGG TGTGGATTAA CCTGCCAGGG AGACAGAGCT CACAATAAAA ATGGCTCAGA 2143
TGCCACTTCA AGAAAAAAA AAA 2166

( 2 ) INFORMATION FOR SEQ ID NO:31:

( i ) SEQUENCE CHARACTERISTICS:
( A ) LENGTH: 501 amino acids
( B ) TYPE: amino acid
( D ) TOPOLOGY: linear ( i i ) MOLECULE TYPE: protein ( x i ) SEQUENCE DESCRIPTION: SEQ ID NO:31:

| | | | | | | | | | | | | | | |
|---|---|---|---|---|---|---|---|---|---|---|---|---|---|---|
|Ser|Gln|Val|Glu|Phe|Leu|Cys|Met|Ser|Leu|Ala|Asn|Pro|Leu|Pro|Thr|
|1| | | |5| | | |10| | | |15| | |
|Asn|Tyr|Thr|Trp|Tyr|His|Asn|Gly|Lys|Glu|Met|Gln|Gly|Arg|Thr|Glu|
| | | |20| | | |25| | | |30| | | |
|Glu|Lys|Val|His|Ile|Pro|Lys|Ile|Leu|Pro|Trp|His|Ala|Gly|Thr|Tyr|
| | |35| | | |40| | | |45| | | | |
|Ser|Cys|Val|Ala|Glu|Asn|Ile|Leu|Gly|Thr|Gly|Gln|Arg|Gly|Pro|Gly|
| |50| | | |55| | | |60| | | | | |
|Ala|Glu|Leu|Asp|Val|Gln|Tyr|Pro|Pro|Lys|Lys|Val|Thr|Thr|Val|Ile|
|65| | | |70| | | |75| | | | | |80| |
|Gln|Asn|Pro|Met|Pro|Ile|Arg|Glu|Gly|Asp|Thr|Val|Thr|Leu|Ser|Cys|
| | | |85| | | |90| | | |95| | | |
|Asn|Tyr|Asn|Ser|Ser|Asn|Pro|Ser|Val|Thr|Arg|Tyr|Glu|Trp|Lys|Pro|
| | | |100| | | |105| | | |110| | | |
|His|Gly|Ala|Trp|Glu|Glu|Pro|Ser|Leu|Gly|Val|Leu|Lys|Ile|Gln|Asn|
| | |115| | | |120| | | |125| | | | |
|Val|Gly|Trp|Asp|Asn|Thr|Thr|Ile|Ala|Cys|Ala|Arg|Cys|Asn|Ser|Trp|
| |130| | | |135| | | |140| | | | | |
|Cys|Ser|Trp|Ala|Ser|Pro|Val|Ala|Leu|Asn|Val|Gln|Tyr|Ala|Pro|Arg|
|145| | | |150| | | |155| | | | | |160| |
|Asp|Val|Arg|Val|Arg|Lys|Ile|Lys|Pro|Leu|Ser|Glu|Ile|His|Ser|Gly|
| | | |165| | | |170| | | |175| | | |
|Asn|Ser|Val|Ser|Leu|Gln|Cys|Asp|Phe|Ser|Ser|His|Pro|Lys|Glu| |
| | | |180| | | |185| | | |190| | | |
|Val|Gln|Phe|Phe|Trp|Glu|Lys|Asn|Gly|Arg|Leu|Leu|Gly|Lys|Glu|Ser|
| | |195| | | |200| | | |205| | | | |

-continued

| Gln | Leu | Asn | Phe | Asp | Ser | Ile | Ser | Pro | Glu | Asp | Ala | Gly | Ser | Tyr | Ser |
|  | 210 |  |  |  | 215 |  |  |  | 220 |  |  |  |  |  |  |

| Cys | Trp | Val | Asn | Asn | Ser | Ile | Gly | Gln | Thr | Ala | Ser | Lys | Ala | Trp | Thr |
| 225 |  |  |  |  | 230 |  |  |  | 235 |  |  |  |  |  | 240 |

| Leu | Glu | Val | Leu | Tyr | Ala | Pro | Arg | Arg | Arg | Val | Ser | Met | Ser | Pro |
|  |  |  |  | 245 |  |  |  |  | 250 |  |  |  | 255 |  |

| Gly | Asp | Gln | Val | Met | Glu | Gly | Lys | Ser | Ala | Thr | Leu | Thr | Cys | Glu | Ser |
|  |  |  | 260 |  |  |  | 265 |  |  |  |  |  | 270 |  |  |

| Asp | Ala | Asn | Pro | Pro | Val | Ser | His | Tyr | Thr | Trp | Phe | Asp | Trp | Asn | Asn |
|  |  | 275 |  |  |  |  | 280 |  |  |  |  | 285 |  |  |  |

| Gln | Ser | Leu | Pro | His | His | Ser | Gln | Lys | Leu | Arg | Leu | Glu | Pro | Val | Lys |
|  | 290 |  |  |  |  | 295 |  |  |  |  | 300 |  |  |  |  |

| Val | Gln | His | Ser | Gly | Ala | Tyr | Trp | Cys | Gln | Gly | Thr | Asn | Ser | Val | Gly |
| 305 |  |  |  |  | 310 |  |  |  |  | 315 |  |  |  |  | 320 |

| Lys | Gly | Arg | Ser | Pro | Leu | Ser | Thr | Leu | Thr | Val | Tyr | Tyr | Ser | Pro | Glu |
|  |  |  |  | 325 |  |  |  |  | 330 |  |  |  |  | 335 |  |

| Thr | Ile | Gly | Arg | Arg | Val | Ala | Val | Gly | Leu | Gly | Ser | Cys | Leu | Ala | Ile |
|  |  |  | 340 |  |  |  |  | 345 |  |  |  | 350 |  |  |  |

| Leu | Ile | Leu | Ala | Ile | Cys | Gly | Leu | Lys | Leu | Gln | Arg | Arg | Trp | Lys | Arg |
|  |  | 355 |  |  |  |  | 360 |  |  |  |  | 365 |  |  |  |

| Thr | Gln | Ser | Gln | Gln | Gly | Leu | Gln | Glu | Asn | Ser | Ser | Gly | Gln | Ser | Phe |
|  | 370 |  |  |  |  |  | 375 |  |  |  | 380 |  |  |  |  |

| Phe | Val | Arg | Asn | Lys | Lys | Val | Arg | Arg | Ala | Pro | Leu | Ser | Glu | Gly | Pro |
| 385 |  |  |  |  | 390 |  |  |  |  | 395 |  |  |  |  | 400 |

| His | Ser | Leu | Gly | Cys | Tyr | Asn | Pro | Met | Met | Glu | Asp | Gly | Ile | Ser | Tyr |
|  |  |  |  | 405 |  |  |  |  | 410 |  |  |  |  | 415 |  |

| Thr | Thr | Leu | Arg | Phe | Pro | Glu | Met | Asn | Ile | Pro | Arg | Thr | Gly | Asp | Ala |
|  |  |  | 420 |  |  |  |  | 425 |  |  |  |  | 430 |  |  |

| Glu | Ser | Ser | Glu | Met | Gln | Arg | Pro | Pro | Arg | Thr | Cys | Asp | Asp | Thr | Val |
|  |  | 435 |  |  |  |  | 440 |  |  |  |  | 445 |  |  |  |

| Thr | Tyr | Ser | Ala | Leu | His | Lys | Arg | Gln | Val | Gly | Asp | Tyr | Glu | Asn | Val |
|  | 450 |  |  |  |  | 455 |  |  |  |  | 460 |  |  |  |  |

| Ile | Pro | Asp | Phe | Pro | Glu | Asp | Glu | Gly | Ile | His | Tyr | Ser | Glu | Leu | Ile |
| 465 |  |  |  |  | 470 |  |  |  |  | 475 |  |  |  |  | 480 |

| Gln | Phe | Gly | Val | Gly | Glu | Arg | Pro | Gln | Ala | Gln | Glu | Asn | Val | Asp | Tyr |
|  |  |  |  | 485 |  |  |  |  | 490 |  |  |  |  | 495 |  |

| Val | Ile | Leu | Lys | His |
|  |  |  |  | 500 |

( 2 ) INFORMATION FOR SEQ ID NO:32:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:32:

Tyr  Arg  Gly  Asp  Arg  Ala  Glu
     1                   5

( 2 ) INFORMATION FOR SEQ ID NO:33:

( i ) SEQUENCE CHARACTERISTICS:
        ( A ) LENGTH: 4 amino acids
        ( B ) TYPE: amino acid
        ( C ) STRANDEDNESS:

(D) TOPOLOGY: linear (i i) MOLECULE TYPE: protein (x i) SEQUENCE DESCRIPTION: SEQ ID NO:33:

Pro Glu Ser Thr
1

(2) INFORMATION FOR SEQ ID NO:34:

(i) SEQUENCE CHARACTERISTICS:
(A) LENGTH: 58 amino acids
(B) TYPE: amino acid
(C) STRANDEDNESS:
(D) TOPOLOGY: linear (i i) MOLECULE TYPE: protein (x i) SEQUENCE DESCRIPTION: SEQ ID NO:34:

| Leu | Ala | Thr | Asp | Met | Ser | Cys | His | Phe | Gln | Gln | Val | Lys | Thr | Met | Lys |
|---|---|---|---|---|---|---|---|---|---|---|---|---|---|---|---|
| 1 | | | | 5 | | | | | 10 | | | | | 15 | |
| Thr | Ala | Leu | Gln | Gln | Leu | Glu | Arg | Ile | Asp | Lys | Ser | Lys | Ala | Leu | Ser |
| | | | 20 | | | | | 25 | | | | 30 | | | |
| Leu | Leu | Leu | His | Ala | Ala | Asp | Ile | Ser | His | Pro | Thr | Lys | Gln | Trp | Ser |
| | | 35 | | | | | 40 | | | | | 45 | | | |
| Trp | His | Ser | Arg | Trp | Thr | Lys | Ala | Leu | Met | | | | | | |
| | 50 | | | | | 55 | | | | | | | | | |

(2) INFORMATION FOR SEQ ID NO:35:

(i) SEQUENCE CHARACTERISTICS:
(A) LENGTH: 125 amino acids
(B) TYPE: amino acid
(C) STRANDEDNESS:
(D) TOPOLOGY: linear (i i) MOLECULE TYPE: protein (x i) SEQUENCE DESCRIPTION: SEQ ID NO:35:

| Ile | Val | Phe | Ser | Ala | Cys | Arg | Met | Pro | Pro | Ser | His | Gln | Leu | Asp | His |
|---|---|---|---|---|---|---|---|---|---|---|---|---|---|---|---|
| 1 | | | | 5 | | | | | 10 | | | | | 15 | |
| Ser | Lys | Leu | Leu | Gly | Tyr | Leu | Lys | His | Thr | Leu | Asp | Gln | Tyr | Val | Glu |
| | | | 20 | | | | | 25 | | | | 30 | | | |
| Ser | Asp | Tyr | Thr | Leu | Leu | Tyr | Leu | His | His | Gly | Leu | Thr | Ser | Asp | Asn |
| | | 35 | | | | | 40 | | | | | 45 | | | |
| Lys | Pro | Ser | Leu | Ser | Trp | Leu | Arg | Asp | Ala | Tyr | Arg | Glu | Phe | Asp | Arg |
| | 50 | | | | | 55 | | | | | 60 | | | | |
| Lys | Tyr | Lys | Lys | Asn | Ile | Lys | Ala | Leu | Tyr | Ile | Val | His | Pro | Thr | Met |
| 65 | | | | | 70 | | | | | 75 | | | | | 80 |
| Phe | Ile | Lys | Thr | Leu | Leu | Ile | Leu | Phe | Lys | Pro | Leu | Ile | Ser | Phe | Lys |
| | | | | 85 | | | | | 90 | | | | | 95 | |
| Phe | Gly | Gln | Lys | Ile | Phe | Tyr | Val | Asn | Tyr | Leu | Ser | Glu | Leu | Ser | Glu |
| | | | 100 | | | | | 105 | | | | | 110 | | |
| His | Val | Lys | Leu | Glu | Gln | Leu | Gly | Ile | Pro | Arg | Gln | Val | | | |
| | | 115 | | | | | 120 | | | | | 125 | | | |